United States Patent
Genovese et al.

(10) Patent No.: US 10,920,196 B2
(45) Date of Patent: Feb. 16, 2021

(54) METHOD FOR SCALABLE SKELETAL MUSCLE LINEAGE SPECIFICATION AND CULTIVATION

(71) Applicants: THE CURATORS OF THE UNIVERSITY OF MISSOURI, Columbia, MO (US); MEMPHIS MEATS, INC., San Leandro, CA (US)

(72) Inventors: Nicholas J. Genovese, Hayward, CA (US); R. Michael Roberts, Columbia, MO (US); Bhanu Prakash V. L. Telugu, College Park, MD (US)

(73) Assignees: The Curators of the University of Missouri, Columbia, MO (US); Memphis Meats, Inc., Berkeley, CA (US)

( * ) Notice: Subject to any disclaimer, the term of this patent is extended or adjusted under 35 U.S.C. 154(b) by 0 days.

(21) Appl. No.: 15/134,252

(22) Filed: Apr. 20, 2016

(65) Prior Publication Data

US 2016/0227830 A1     Aug. 11, 2016

Related U.S. Application Data

(63) Continuation of application No. PCT/US2014/063250, filed on Oct. 30, 2014.

(60) Provisional application No. 61/962,068, filed on Oct. 30, 2013.

(51) Int. Cl.
| | | |
|---|---|---|
| C12N 5/077 | (2010.01) | |
| A23L 13/00 | (2016.01) | |
| C12N 5/10 | (2006.01) | |

(52) U.S. Cl.
CPC ........... *C12N 5/0658* (2013.01); *A23L 13/00* (2016.08); *C12N 5/10* (2013.01); *A23V 2002/00* (2013.01); *C12N 2501/392* (2013.01); *C12N 2501/40* (2013.01); *C12N 2501/415* (2013.01); *C12N 2501/60* (2013.01); *C12N 2501/602* (2013.01); *C12N 2501/603* (2013.01); *C12N 2501/604* (2013.01); *C12N 2501/72* (2013.01); *C12N 2501/727* (2013.01); *C12N 2501/999* (2013.01); *C12N 2506/02* (2013.01); *C12N 2506/45* (2013.01)

(58) Field of Classification Search
CPC . C12N 5/0658–5/0661; C12N 2506/45; C12N 2506/1346–2506/1392; C12N 15/635; C12N 15/8238; C12N 2501/60–2501/608; C12N 2506/02; C12N 2506/03; C12N 2506/13; C12N 5/0652; C12N 2501/603; C12N 2501/604; C12N 2501/415; A23L 1/31; A23L 13/00

See application file for complete search history.

(56) References Cited

U.S. PATENT DOCUMENTS

| | | |
|---|---|---|
| 5,624,840 A | 4/1997 | Naughton et al. |
| 6,835,390 B1 | 12/2004 | Vein |
| 7,147,871 B2 | 12/2006 | Voytik-Harbin et al. |
| 7,270,829 B2 | 9/2007 | Van Eelen |
| 8,703,216 B2 | 4/2014 | Forgacs et al. |
| 8,883,502 B2 | 11/2014 | Kumar |
| 2006/0121006 A1 | 6/2006 | Chancellor et al. |
| 2007/0248716 A1 | 10/2007 | Kruse et al. |
| 2010/0319079 A1 | 12/2010 | Kruse et al. |
| 2011/0091604 A1 | 4/2011 | Miller |
| 2011/0191871 A1 | 8/2011 | Walsh et al. |
| 2011/0301249 A1 | 12/2011 | Challakere |
| 2013/0004466 A1 | 1/2013 | Tremblay et al. |
| 2013/0029008 A1 | 1/2013 | Forgacs et al. |
| 2013/0255003 A1 | 10/2013 | Forgacs et al. |
| 2014/0093618 A1 | 4/2014 | Forgacs et al. |
| 2014/0242155 A1 | 8/2014 | Ramunas et al. |
| 2014/0370537 A1 | 12/2014 | Sakurai et al. |
| 2015/0079238 A1 | 3/2015 | Marga et al. |
| 2015/0087532 A1 | 3/2015 | Brown et al. |
| 2015/0289541 A1 | 10/2015 | Brown et al. |
| 2015/0296834 A1 | 10/2015 | Geistlinger |
| 2015/0296835 A1 | 10/2015 | Anderson et al. |
| 2015/0305361 A1 | 10/2015 | Holtz-Schietinger et al. |
| 2015/0305390 A1 | 10/2015 | Vrljic et al. |
| 2016/0251625 A1 | 9/2016 | Genovese et al. |
| 2019/0024079 A1 | 1/2019 | Genovese et al. |

FOREIGN PATENT DOCUMENTS

| | | |
|---|---|---|
| CA | 2333966 C | 12/1999 |
| CA | 2780087 A1 | 12/2012 |
| CN | 1942576 A | 4/2007 |
| CN | 101624570 A | 1/2010 |

(Continued)

OTHER PUBLICATIONS

Yokoyama et al. The myogenic transcriptional network. Cellular and Molecular Life Sciences, vol. 68, pp. 1843-1849, Feb. 2011.*

(Continued)

*Primary Examiner* — Jennifer Dunston

(74) *Attorney, Agent, or Firm* — Cooley LLP

(57) ABSTRACT

The present disclosure relates to methods for enhancing cultured meat production, such as livestock-autonomous meat production. In certain aspects, the meat is any metazoan tissue or cell-derived comestible product intended for use as a comestible food or nutritional component by humans, companion animals, domesticated or captive animals whose carcasses are intended for comestible use, service animals, conserved animal species, animals used for experimental purposes, or cell cultures.

11 Claims, 27 Drawing Sheets

Specification includes a Sequence Listing.

(56) References Cited

FOREIGN PATENT DOCUMENTS

| EP | 0435617 A | 7/1991 | | |
|---|---|---|---|---|
| EP | 1037966 B1 | 5/2003 | | |
| JP | 2013-81783 | 5/2013 | | |
| WO | WO-1993/009236 A | 5/1993 | | |
| WO | WO-1999/031222 A1 | 6/1999 | | |
| WO | WO-1999/031223 A1 | 6/1999 | | |
| WO | WO-2006/041429 A2 | 4/2006 | | |
| WO | WO-2010-068897 A2 | 6/2010 | | |
| WO | WO-2012/176023 A1 | 12/2012 | | |
| WO | WO 2012170995 A2 * | 12/2012 | ........... | C12N 5/0696 |
| WO | WO-2013/016547 A2 | 1/2013 | | |
| WO | WO 2013073246 A1 * | 5/2013 | ........... | C12N 5/0658 |
| WO | WO-2015/066377 A1 | 5/2015 | | |
| WO | WO-2017-019125 A1 | 2/2017 | | |
| WO | WO-2017/124100 A1 | 7/2017 | | |
| WO | WO-2018/208628 A1 | 11/2018 | | |
| WO | WO-2019/014652 A1 | 1/2019 | | |

OTHER PUBLICATIONS

McFarlane et al. Myostatin signals through Pax7 to regulate satellite cell self-renewal. Experimental Cell Research, vol. 314, pp. 317-329, 2008, available online Sep. 2007.*

Maak et al. Identification and analysis of putative regulatory sequences for the MYF5/MYF6 locus in different vertebrate species. Gene, vol. 379, pp. 141-147, May 2006.*

Wagers, AJ. Wnt Not, Waste Not. Cell Stem Cell, vol. 2, pp. 6-7, 2008.*

Li et al. Short-term serum-free culture reveals that inhibition fo Gsk3beta induces the tumor-like growth fo mouse embryonic stem cells. PLoS ONE, vol. 6, No. 6, e21355, Jun. 23, 2011, printed as pp. 1/10-10/10.*

Lian et al. Directed cardiomyocyte differentiation from human pluripotent stem cells by modulating Wnt/beta-catenin signaling under fully defined conditions. Nature Protocols, vol. 8, No. 1, pp. 162-175, 2013, published online Dec. 20, 2012.*

Tan et al. Efficient derivation of lateral plate and paraxial mseoderm subtypes from human embryonic stem cells through GSKi-mediated differentiation. Stem Cells and Development, vol. 22, No. 13, pp. 1893-1906, Feb. 2013.*

Chen et al. Potentiation of MyoD1 activity by 5-aza-2'-deoxycytidine. Cell Growth & Differentiation, vol. 1, pp. 383-392, Aug. 1990.*

Ozasa et al. Efficient conversion of ES cells into myogenic lineage using the gene-inducible system. Biochemical and Biophysical Research Communications, vol. 357, pp. 957-963, Apr. 2007.*

Cenciarelli et al. Critical role played by cyclin D3 in the MyoD-mediated arrest of cell cycle during myoblast differentiation. Molecular and Cellular Biology, vol. 19, No. 7, pp. 5203-5217, Jul. 1999.*

Lavial et al. Chicken embryonic stem cells as a non-mammalian embryonic stem cell model. Development, Growth & Differentiation, vol. 52, pp. 101-1114, 2010.*

Taylor et al. Multiple new phenotypes induced in 10T1/2 and 3T3 cells treated with 5-azacytidine. Cell, vol. 17, pp. 771-779, Aug. 1979.*

Baquero-Perez et al. A simplified but robust method for the isolation of avian and mammalian satellite cells. BMC Cell Biology, vol. 13:16, Jun. 12, 2012, printed as pp. 1/11-11/11.*

Rezanejad et al. Induced pluripotent stem cells: Progress and future perspectives in the stem cell world. Cellular Reprogramming, vol. 14, No. 6, pp. 459-470, Oct. 4, 2012.*

Weintraub et al. Activation of muscle-specific genes in pigment, nerve, fat, liver and fibroblast cell lines by forced expression of MyoD. Proceedings of the National Academy of Sciences, USA, vol. 86, pp. 5434-5438, Jul. 1989.*

Hanas et al. Potentiation of myogenesis by 5-azacytidine. Journal of Cell Biology, vol. 91, No. 2, p. 27, Abstract 1051, Nov. 1981.*

Rinkevich, B. Cell cultures from marine invertebrates: New insights for capturing endless stemness. Marine Biotechnology (New York, N.Y.), vol. 13, No. 3, pp. 345-354, Jun. 2011, Epub Jan. 7, 2011. (Year: 2011).*

Nowak-Imialek et al. Pluripotent cells in farm animals: state of the art and future perspectives. Reproduction, Fertility and Development, vol. 25, No. 1, pp. 103-108, 2012. (Year: 2012).*

Blomberg et al. Twenty years of embryonic stem cell research in farm animals. Reproduction in Domestic Animals, vol. 47, Suppl. 4, pp. 80-85, Aug. 2012. (Year: 2012).*

Molkentin et al. Cooperative activation of muscle gene expression by MEF2 and myogenic bHLH proteins. Cell, vol. 83, pp. 1125-1136, Dec. 1995. (Year: 1995).*

Hupkes et al. Epigenetics: DNA demethylation promotes skeletal myyotube maturation. The FASEB Journal, vol. 25, No. 11, pp. 3861-3872, Nov. 2011. (Year: 2011).*

Chen et al. DNA methyltransferase inhibitor CDA-II inhibits myogenic differentiation. Biochemical and Biophysical Research Communications, vol. 422, pp. 522-526, May 22, 2012. (Year: 2012).*

Tseng et al. The GSK-3 inhibitor BIO promotes proliferation in mammalian cardiomyocytes. Chemistry & Biology, vol. 13, pp. 957-963, Sep. 2006. (Year: 2006).*

Park et al. Generation of porcine induced pluripotent stem cells and evaluation of their major histocompatibility complex protein expression in vitro. Veterinary Research Communications, vol. 37, No. 4, pp. 293-301, Dec. 2013, published online Aug. 23, 2013. (Year: 2013).*

West et al. Porcine induced pluripotent stem cells produce chimeric offspring. Stem Cells and Development, vol. 19, No. 8, 2010, pp. 1211-1220, 2010. (Year: 2010).*

International Preliminary Report on Patentability in corresponding PCT Application No. PCT/US2014/063250, dated May 3, 2016, Form PCT/IB/373 only.

International Search Report and Written Opinion in corresponding PCT Application No. PCT/US2014/063250, dated Jan. 21, 2015.

International Search Report in corresponding PCT Application No. PCT/US2014/063250, dated Jan. 21, 2015.

Albini, S., et al., "Epigenetic Reprogramming of Human Embryonic Stem Cells into Skeletal Muscle Cells and Generation of Contractile Myospheres," Cell Reports 3:661-670 (2013).

Barberi, T., et al., "Derivation of Engraftable Skeletal Myoblasts from Human Embryonic Stem Cells," Nature Medicine 13(5):642-648(2007).

Bartholet, J., "Inside the Meat Lab a Handful of Scientists Aim to Satisfy the World's Growing Appetite for Steak Without Wrecking the Planet. The First Step: Grab a Petri Dish," Scientific American, pp. 65-69 (2011).

Benjaminson, M., et al.,"In Vitro Edible Muscle Protein Production System (MPPS): Stage 1, FISH," Acta Astronautica 51(12):879-889 (2002).

Bentzinger, C., et al., "Building Muscle: Molecular Regulation of Myogenesism," Cold Spring Harb Perspect Biol 4(2):1-16 (2012).

Bhagavati and Xu., "Generation of Skeletal Muscle from Transplanted Embryonic Stem Cells in Dystrophic Mice," Biochemical and Biophysical Research Communications 333:644-649 (2005).

Bhat and Bhat, "Animal-Free Meat Biofabrication," American Journal of Food Technology 6(6):441-459, (2011).

Boonen and Post, "The Muscle Stem Cell Niche: Regulation of Satellite Cells During Regeneration," Tissue Engineering—Part B: Reviews 14(4):419-431 (2008).

Chang, et al., "Generation of Transplantable, Functional Satellite-Like Cells from Mouse Embryonic Stem Cells," FASEB J. 23, 1907-1919 (2009).

Chiu and Blau,"5-5 Azacytidine Permits Gene Activation in a Previously Noninducible Cell Type," Cell, vol. 40, 417-424 (1985).

Darabi, R., et al, "Perspective Lineage-Specific Reprogramming as a Strategy for Cell Therapy," Cell Cycle 7(12):1732-1737 (2008).

Darabi, R., et al., "Assessment of the Myogenic Stem Cell Compartment Following Transplantation of Pax3/Pax7-Induced Embryonic Stem Cell-Derived Progenitors," Lillehei Heart Institute, Department of Medicine, University of Minnesota, Minneapolis, MN, USA, 27 pages (2011).

(56) References Cited

OTHER PUBLICATIONS

Darabi, R., et al., Functional Skeletal Muscle Regeneration From Differentiating Embryonic Stem Cells, Nature and Medicine 14(2):134-143 (2008).
Datar and Betti, "Possibilities for an In Vitro Meat Production System," Innovative Food Science & Emerging Technologies 11(1):13-22(2010).
Davis, R., et al., "Expression of a Single Transfected cDNA Converts Fibmblasts to Myoblasts," Cell, vol. 51. 987-1000 (1987).
Dekel, I., et al., "Conditional Conversion of ES Cells to Skeletal Muscle by an Exogenous MyoDl Gene," (1992).
Edelman, P., et al., "In Vitro-Cultured Meat Production," Tissue Engineering 11(5/6):659-662 (2005).
Gianakopoulos, P., et al., "MyoD Directly Up-regulates Premyogenic Mesoderm Factors during Induction of Skeletal Myogenesis in Stem Cells," The Journal of Biological Chemistry 286(4):2517-2525 (2011).
Goudenege, S., et al., "Myoblasts Derived From Normal hESCs and Dystrophic hiPSCs Efficiently Fuse With Existing Muscle Fibers Following Transplantation," Molecular Therapy 20(11):2153-2167 Nov. 2012 (2012).
Hollenberg, S., et al., "Use of a conditional MyoD transcription factor in studies of MyoD trans-activation and muscle determination," Proc. Natl. Acad. Sci. USA vol. 90, pp. 8028-8032 1993).
Hopkins and Dacey, "Vegetarian meat: Could Technology Save Animals and Satisfy Meat Eaters?" Journal of Agricultural and Environmental Ethics 21(6):579-596 (2008).
Hwang, Y., et al., "Directed In Vitro Myogenesis of Human Embryonic Stem Cells and Their In Vivo Engraftment," PLOS ONE e72023 8(8):1-10 (2013).
Iacovino, M., et al., "Inducible Cassette Exchange: A Rapid and Efficient System Enabling Conditional Gene Expression in Embryonic Stem and Primary Cells," Stem Cells 2011;29:1580-1587 (2011).
Jones, N., "A Taste of Things to Come?" Nature 468:752-753 (2010).
Lassar, A., et al., "Transfection of a DNA Locus That Mediates the Conversion of IOTV2 Fibroblasts to Myoblasts," Cell 47:649-656 (1986).
Leung, M., et al., "Nanofiber-Based in Vitro System for High Myogenic Differentiation of Human Embryonic Stem Cells," Biomacromolecules 14:4207-4216 (2013).
Mahmood, A., Enhanced Differentiation of Human Embryonic Stem Cells to Mesenchymal Progenitors by Inhibition of TGF-beta/Activin/Nodal Signaling Using SB-431542 Journal of Bone and Mineral Research 25(6):1216-1233 (2010).
Minzuno, Y., et al., "Generation of Skeletal Muscle Stem/Progenitor Cells from Murine Induced Pluripotent Stem Cells," The FASEB Journal 24:2245-2243 (2010).
Post, M., "Cultured beef: Medical Technology to Produce Food," Journal of the Science of Food and Agriculture 94(6):1039-1041 (2014).
Post, M., "Cultured Meat From Stem Cells: Challenges and Prospects," Meat Sci. 92(3):297-301 (2012).
Rao, L., et al., "Highly Efficient Derivation of Skeletal Myotubes from Human Embryonic Stem Cells," Stem Cell Rev and Rep 8:1109-1119 (2012).
Rohwedel, J., et al., "Muscle Cell Differentiation of Embryonic Stem Cells Reflects Myogenesis In Vivo: Developmentally Regulated Expression of Myogenic Determination Genes and Functional Expression of Ionic Currents.," Dev Biol. 164(1):87-101 (1994). (Abstract).
Rommel, C., "Mediation of IGF-1-Induced Skeletal Myotube Hypertrophy by PI(3)K/Akt/mTOR and PI(3)K/Akt/GSK3 Pathways," Nature Cell Biology 3:1009-1013 (2001).
Ryan, T., "Retinoic Acid Enhances Skeletal Myogenesis in Human Embryonic Stem Cells by Expanding the Premyogenic Progenitor Population," Stem Cell Rev and Rep 8:482-493 (2012).

Sakurai, H., et al., "Paraxial Mesodermal Progenitors Derived from Mouse Embryonic Stem Cells Contribute to Muscle Regeneration via Differentiation into Muscle Satellite Cells," Stem Cells 26:1865-1873 (2008).
Sakurai, H., et al., "Bidirectional Induction Toward Paraxial Mesodermal Derivatives from Mouse ES Cells in Chemically Defined Medium," Stem Cell Research 3:157-169 (2009).
Salani, S., et al., "Generation of Skeletal Muscle Cells from Embryonic and Induced Pluripotent Stem Cells as an In Vitro Model and for Therapy of Muscular Dystrophies," J. Cell. Mol. Med. 16(7):1353-1364 (2012).
Sasaki, T., et al., "Generation of a Multi-Layer Muscle Fiber Sheet from Mouse ES Cells by the Spermine Action at Specific Timing and Concentration," Differentiation 76:1023-1030(2008).
Telugu, B., et al., "Lif-Dependent, Pluripotent Stem Cells Established From Inner Cell Mass of Porcine Embryos," The American Society for Biochemistry and Molecular Biology, Inc. ,Downloaded from www.jbc.org at University of Missouri-Columbia, on Jul. 15, 2011 (2011).
Tuomisto, et al., "Environmental Impacts of Cultured Meat Production," Environ. Sci. Technol. 45(14):6117-6123 (2011).
Van der Schaft, D., et al., "Engineering Skeletal Muscle Tissues From Murine Myoblast Progenitor Cells and Application of Electrical Stimulation," J. Vis. Exp. 73:1-6 (2013)).
Van der Velden, J., et al., "Inhibition of Glycogen Synthase Kinase-3beta-activity is Sufficient to Stimulate Myogenic Differentiation," Am J Physiol Cell Physiol 290: C453-C462, (2006).
Van Der Weele, C., "In Vitro Meat," Encyclopedia of Food and Agricultural Ethics, pp. 1-8 (2014).
Van Der Weele, C., "In Vitro Meat: Promises and Responses: Cooperation Between Science, Social Research and Ethics," Global Food Security: Ethical and Legal Challenges: EurSafe 2010 Bilbao, Spain Sep. 16-18, 2010, pp. 507-512.
Vyas, D., et al., " GSK-3 Negatively Regulates Skeletal Myotube Hypertrophy," Am J Physiol Cell Physiol 283: C545-C551 (2002).
Wilschut, K., et al., "Alpha 6 Integrin is Important for Myogenic Stem Cell Differentiation," Stem Cell Research 7:112-123 (2011).
Wilschut, K., et al., "Extracellular Matrix Components Direct Porcine Muscle Stem Cell Behavior," Experimental Cell Research 316:341-352 (2010).
Wilschut, K., et al., "Isolation and Characterization of Porcine Adult Muscle-Derived Progenitor Cells," Journal of Cellular Biochemistry 105:1228-1239 (2008).
Wu, G., et al., "Production and Supply of High-Quality Food Protein for Human Consumption: Sustainability, Challenges, and Innovations," Annals of the New York Academy of Sciences 1321(1):1-19 (2014).
Zheng, J., K., et al., "Skeletal Myogenesis by Human Embryonic Stem Cells," Cell Research 713-722 (2006).
Tanaka, et al., "Efficient and Reproducible Myogenic Differentiation from Human iPS Cells: Prospects for Modeling Miyoshi Myopathy In Vitro," PLOS ONE e61540 8(4):1-14 (2013).
Langelaan, et al., "Meet the New Meat: Tissue Engineered Skeletal Muscle," Trends in Food Science & Technology 21:59-66 (2010).
Genovese et al.,"Enhanced Development of Skeletal Myotubes form Porcine Induced Pluripotent Stem Cells," Scientific Reports, vol. 7, 12 pages (2017).
Extended European Search Report dated May 19, 2017, from the European patent Office for Application No. 14858383.4, filed Oct. 30, 2014, 10 pages.
Iemata, M., et al., "Suppression by Glutamate of Proliferative Activity Through Glutathione Depletion Mediated by the Cystine/Glutamate Antiporter in Mesenchymal C3H10T1/2 Stem Cells," Journal of Cellular Physiology 213:721-729 (2007).
A. The English translation of paragraph 2 on p. 152 to paragraph 1 on p. 157 of Ref C3.
Hu, Yang "Exercise molecule biology," Beijing Sport University press, pp. 152-157 (2013).
B. The English translation of paragraphs 4-8 on p. 372 of Ref C5.
Yu et al., "Chinese Disease Signal Pathway and Targeted Therapy," Anhui Science and Technology Press, p. 372 (2013).

(56) References Cited

OTHER PUBLICATIONS

Nagashima et al., "The Hippo Pathway as Drug Targets in Cancer Therapy and Regenerative Medicine," Current Drug Targets, (2017), vol. 18, pp. 447-454.

Wang et. al., "Immortalization of chicken preadipocytes by retroviral transduction of chicken TERT and TR," (2017), PLoS ONE 12(5): e0177348. retrieved May 9, 2017 at https://doi.org/10.1371/journal.pone.0177348.

Jesus et. al., "The telomerase activator TA-65 elongates short telomeres and increases health span of adult /old mice without increasing cancer incidence," Aging Cell 10:604-621 (2011).

Bell et. al., "Understanding TERT Promoter Mutations: A Common Path to Immortality," Mol Cancer Res 14:315-323 (2016). Published OnlineFirst Mar. 3, 2016, retrieved Jul. 6, 2017 from mcr.aacrjournals.org, 10 pages.

Dominguez et. al., "Beyond editing: repurposing CRISPR—Cas9 for precision genome regulation and interrogation," Nature Reviews Molecular Cell Biology 17:5-15 (2016).

Liu et. al., "Linking Telomere Regulation to Stem Cell Pluripotency," Trends in Genetics 33(1): 16-33 (2017).

International Search Report and Written Opinion issued by the International Searching Authority for Application No. PCT/US17/13782, dated Apr. 10, 2017, 7 pages.

Pandurangan, et al. A novel approach for in vitro meat production. Appl Microbiol Biotechnol. Jul. 2015; 99(13):5391-5395. doi: 10.1007/s00253-015-6671-5. Epub May 14, 2015.

Munro, et al. Histone deacetylase inhibitors induce a senescence-like state in human cells by a p16-dependent mechanism that is independent of a mitotic clock. Exp Cell Res. 2004 295(2):525-538.

Sharpless, et al. Forging a signature of in vivo senescence. Nature Reviews Cancer 2015, 15(7):397-408.

Harley. Telomerase is not an oncogene. Oncogene 2002, 21(4):494-502.

Garrels et al. Ectopic expression of human telomerase KNA component results In increased telomerase activity and elongated telomeres in bovine blastocysts. Biol Reprod. 2012, 87(4):95, 1-7.

Barnes, et al., Advances in animal cell recombinant protein production: GS-NS0 expression system, Cytotechnology 2000, vol. 32, pp. 109-123.

Canizo et al., "Exogenous human OKSM factors maintain pluripotency gene expression of bovine and porcine iPS-like cells obtained with STEMCCA delivery system," BMC Research Notes vol. 11, Article No. 509 (2018), 8 pages.

Telugu, B., et al., "Leukemia Inhibitory Factor (LIF)-dependent, Pluripotent Stem Cells Established from Inner Cell Mass of Porcine Embryos," Journal of Biological Chemistry, 2011, 286(33):28948-28953.

Black, Brian L., and Eric N. Olson. "Transcriptional control of muscle development by myocyte enhancer factor-2 (MEF2) proteins" Annual review of cell and developmental biology 14.1 (1998): 167-196.

Choi, Sang-Woon, and Simonetta Friso. "Epigenetics: a new bridge between nutrition and health" Advances in nutrition 1.1 (2010): 8-16.

Desbois-Mouthon, Christele, et al. "Insulin and IGF-1 stimulate the β-catenin pathway through two signalling cascades involving GSK-3β inhibition and Ras activation" Oncogene 20.2 (2001): 252-259.

Ding, Vanessa MY, et al. "FGF-2 modulates Wnt signaling in undifferentiated hESC and iPS cells through activated PI3-K/GSK3β signaling" Journal of cellular physiology 225.2 (2010): 417-428.

Hupkes, Marlinda, et al. "DNA methylation restricts spontaneous multi-lineage differentiation of mesenchymal progenitor cells, but is stable during growth factor-induced terminal differentiation" Biochimica et Biophysica Acta (BBA)-Molecular Cell Research 1813.5 (2011): 839-849.

Schnapp, Esther, et al. "Induced early expression of mrf4 but not myog rescues myogenesis in the myod/myf5 double-morphant zebrafish embryo" Journal of Cell Science 122.4 (2009): 481-488.

* cited by examiner

DOX = Doxycycline ; E2 = 17β-Estradiol; TRE = Tetracycline Responsive Element; rTA = tetracycline transactivator; MBS = MyoD Binding Site

SEQUENCE LISTING

```
<160> NUMBER OF SEQ ID NOS: 1

<210> SEQ ID NO 1
<211> LENGTH: 1905
<212> TYPE: DNA
<213> ORGANISM: Artificial Sequence
<220> FEATURE:
<223> OTHER INFORMATION: Synthetic fusion

<400> SEQUENCE: 1
atggagcttc tatcgccgcc actccgggac atagacttga caggcccga cggctctctc      60 tgctcctttg agacagcaga cgacttctat gatgaccgt gtttcgactc accagacctg     120
cgcttttttg aggacctgga cccgcgcctg gtgcacatgg gagccctcct gaaaccggag     180
gagcacgcac acttccctac tgcggtgcac ccaggccag gcgctcgtga ggatgagcat     240
gtgcgcgcgc ccagcgggca ccaccaggcg ggtcgctgct tgctgtgggc ctgcaaggcg     300
tgcaagcgca agaccaccaa cgctgatcgc cgcaaggccg ccaccatgcg cgagcgccgc     360
cgcctgagca aagtgaatga ggccttcgag acgctcaagc gctgcacgtc cagcaacccg     420
aaccagcggc tacccaaggt ggagatcctg cgcaacgcca tccgctacat cgaaggtctg     480
caggctctgc tgcgcgacca ggacgccgcg cccctggcg attctgctgg agacatgaga     540
gctgccaacc tttggccaag cccgctcatg atcaaacgct ctaagaagaa cagcctggcc     600
ttgtccctga cggccgacca gatggtcagt gccttgttgg atgctgagcc ccccatactc     660
tattccgagt atgatcctac cagacccttc agtgaagctt cgatgatggg cttactgacc     720
aacctggcag acagggagct ggttcacatg atcaactggg cgaagagggt gccaggcttt     780
```

-continued

```
gtggatttga ccctccatga tcaggtccac cttctagaat gtgcctggct agagatcctg    840
atgattggtc tcgtctggcg ctccatggag cacccaggga agctactgtt tgctcctaac    900
ttgctcttgg acaggaacca gggaaaatgt gtagagggca tggtggagat cttcgacatg    960
ctgctggcta catcatctcg gttccgcatg atgaatctgc agggagagga gtttgtgtgc   1020
ctcaaatcta ttattttgct taattctgga gtgtacacat ttctgtccag caccctgaag   1080
tctctggaag agaaggacca tatccaccga gtcctggaca agatcacaga cactttgatc   1140
cacctgatgg ccaaggcagg cctgaccctg cagcagcagc accagcggct ggcccagctc   1200
ctcctcatcc tctcccacat caggcacatg agtaacaaag gcatggagca tctgtacagc   1260
atgaagtgca agaacgtggt gcccctctat gacctgctgc tggagatgct ggacgcccac   1320
cgcctacatg cgcccactag ccgtggaggg gcatccgtgg aggagacgga ccaaagccac   1380
ttggccactg cgggctctac ttcatcgcat tccttgcaaa agtattacat cacgggggag   1440
gcagagggtt tccctgccac agctatcgcc gctgccttct acgcacctgg accgctgccc   1500
ccaggccgtg gcagcgagca ctacagtggc gactcagatg catccagccc gcgctccaac   1560
tgctctgatg gcatgatgga ttacagcggc cccccaagcg gcccccggcg gcagaatggc   1620
tacgacaccg cctactacag tgaggcggcg cgcgagtcca ggccagggaa gagtgcggct   1680
gtgtcgagcc tcgactgcct gtccagcata gtggagcgca tctccacaga cagcccgct   1740 gcgcctgcgc tgcttttggc agatgcacca ccagagtcgc ctccgggtcc gccagagggg   1800
gcatccctaa gcgacacaga acagggaacc cagaccccgt ctcccgacgc cgcccctcag   1860
tgtcctgcag gctcaaaccc caatgcgatt tatcaggtgc tttga                    1905
```

METHOD FOR SCALABLE SKELETAL MUSCLE LINEAGE SPECIFICATION AND CULTIVATION

STATEMENT REGARDING FEDERALLY-SPONSORED RESEARCH AND DEVELOPMENT

This invention was made with Government support under Grant No. RO1 HD069979 awarded by the National Institutes of Health. The Government has certain rights in the invention.

INCORPORATION OF SEQUENCE LISTING

The content of the electronically submitted sequence listing in ASCII text file (Name 52553_136621_ST25.txt; Size: 2,962 bytes; and Date of Creation: Oct. 30, 2014) filed with the application is incorporated herein by reference in its entirety.

BACKGROUND

The present disclosure relates to methods for enhancing cultured meat production, such as livestock-autonomous meat production. The conceptual promises of "cultured meat" (e.g., animal-autonomous meat production by in vitro cell culture, tissue engineering, and food technology methods) include increased production efficiency, reduced environmental impacts, expanded culinary application utility, enhanced nutritional value, cruelty-free production and improved food safety relative to conventionally produced meats. Technologies, to date however, have not advanced sufficiently to support scalable, economically sustainable production. The current laboratory-scale cultivation of prototype tissues has utilized primary animal components such as animal tissues and serum, thereby largely negating the advantages of animal-autonomous meat production. Hence, current methods fail to resolve the animal dependence from cultured meat production sufficiently to realize the conceptual promises of "cultured meat" and provide a commercially advantageous product. Therefore, there is a need to provide new and improved methods for scalable meat cultivation from a self-renewing source in vitro for dietary nutrition and other applications.

SUMMARY

The example embodiments provide a scalable platform for skeletal muscle cultivation that utilizes cell lines with the potential to differentiate as skeletal muscle. In certain aspects, the cell lines are from livestock such as domestic cattle, pigs, sheep, goats, camels, water buffalo, rabbits and the like. In certain aspects, the cells lines are from poultry such as domestic chicken, turkeys, ducks, geese, pigeons and the like. In certain aspects, the cell lines are from common game species such as wild deer, gallinaceous fowl, waterfowl, hare and the like. In certain aspects, the cell lines are from aquatic species or semi-aquatic species harvested commercially from wild fisheries or aquaculture operations, or for sport, including certain fish, crustaceans, mollusks, cephalopods, cetaceans, crocodilians, turtles, frogs and the like. In certain aspects, the cell lines are from exotic, conserved or extinct animal species. In certain aspects, the cell lines are from any metazoan species demonstrating the capacity for skeletal muscle tissue specification. In certain aspects, the cell lines are for research or for therapeutic purposes, such as humans, primates, rodents including rats and mice, and companion animals such as dogs, cats, horses, and the like. In certain specific aspects, the cell lines from any organisms are self-renewing stem cell lines. In certain aspects, the selected cell line is modified by a 'genetic switch' to induce rapid and efficient conversion of cells to skeletal muscle for cultured meat production. In an example embodiment, the above or other aspects may be accomplished by a method comprising modifying a selected self-renewing cell line by a myogenic transcription factor to produce a myogenic-transcription-factor-modified cell line, and inducing such modified cell line by exogenous regulation to direct alternate self-renewal or differentiation processes.

In certain aspects, the self-renewing cell line is selected from a group consisting of embryonic stem cells, induced pluripotent stem cells, somatic cell lines, or extra-embryotic cell lines with myogenic potential. In certain aspects, the cell line is derived from species intended for dietary consumption. Illustrative, non-limiting examples of myogenic transcription factors include, alone or in combination, MYOD1, MYOG, MYF5, MYF6, PAX3, PAX7, paralogs, orthologs, genetic variants thereof, or transcriptional activation agonists of the respective promoter recognition DNA sequences of the myogenic transcription factors as further described herein.

In certain specific aspects, an inducible MyoD transcription factor may be used as the differentiation lineage specifier. In certain specific aspects, the porcine induced pluripotent cell line O2K may be employed as the self-renewing cell line. In one specific aspect the method comprises modifying a O2K stem cell line with an inducible MyoD transcription factor to produce a myogenic-transcription-factor-modified O2KM cell line, and inducing such O2KM cell line by exogenous regulation to direct self-renewal or differentiation processes. The aforementioned modifying step can further comprise modifying the cell line with a chromosomally integrated vector constitutively expressing an inducible fusion of the MYOD1 transcription factor and an ESR1 ligand binding domain from a constitutively active promoter region. For example, the inducible activity of the translated fusion transcript (e.g., MyoDER), can be conditionally activated in the presence of the ESR1 agonist (e.g., 17-β Estradiol (E2)).

In certain aspects, the inducing step can further comprise the self-renewal sub-step and the differentiation sub-step regulated by a double-switch mechanism. In the self-renewal sub-step, the modified cell line undifferentiated ground-state is preserved, such as in the presence of doxycycline (DOX), whereby the cell line is maintained in a stem cell self-renewal state by the induced expression of the pluripotency transgenes POU5F1 and KLF4. In the differentiation sub-step, the modified cell line is treated, such as with E2 in the absence of DOX, whereas the cell line is efficiently specified to skeletal myocytes, i.e., the myogenic lineage, by the inducible MyoD transcription factor, resulting in characteristic elongated cells with spindle-like morphology. When further cultured in low-mitogen culture medium, the derivative myocytes can fuse into multinucleated myotubes, precursors to skeletal muscle fibers. Following extended culture in low-mitogen medium, the multinucleated myotubes mature into skeletal muscle fibers capable of terminal differentiation, as evidenced by increased expression of MYOG, DES, MYHC; fusion; and development of sarcomeric myofibrils with contractile potential. The differentiation sub-step can further comprise adding certain reagents in the culture medium for activating the canonical WNT signaling pathway to prevent cell death and facilitate myogenic differentiation, and adding epigenetic modulators to the culture medium to alter the chromatin structure for enhanced myogenic gene expression.

Certain aspects of the disclosure employ genetically enhanced cells for unlimited renewal capacity and efficient conversation to skeletal muscle, the predominant tissue lineage constituting non-offal meat products, in serum-free culture medium. When coupled with a scalable tissue engineering approach, such methods can revolutionize the way meat is produced and marketed for consumers by enabling cultivation of animal tissue in unlimited quantities for animal-autonomous cultured meat production. Additional applications contemplated include in vivo xeno-transplantation use and in vitro models for drug screening, developmental physiology, and developmental biology.

Further features and advantages of the disclosure, as well as the structure and operation of various embodiments of the disclosure, are described in detail below with reference to any accompanying drawings.

BRIEF DESCRIPTION OF THE DRAWINGS/FIGURES

FIG. 1. FIG. 1 shows a MyoDER DNA sequence (SEQ ID NO:1).

FIG. 2 is a schematic illustration of a method comprising a double-switch regulation mechanism for expansion of the undifferentiated cell line, or skeletal muscle lineage specification.

FIG. 3. FIG. 3 is a schematic illustration showing a double-switch mechanism applied to the myogenic modified 02KM cell line regulated by DOX or E2. Panel A shows the 02KM cell self-renewal milieu, and Panel B shows the 02KM myogenic differentiation milieu.

FIG. 4A is a schematic illustration of the selectable MyoDER transgene expression cassette. Arrows and boxes respectively indicate promoter and gene sequences.

FIG. 4B shows Western blot image detection of MyoDER transgene expression in blasticidin-selected O2K by an anti-MYOD1 antibody. Transgene expression cassette modified O2K is designated as O2KM. TUBA (alpha-tubulin) is detected as an internal loading control.

FIG. 5 is an image showing O2KM cells exhibiting stable, compact-colony morphology in self-renewal conditions as the parental O2K cell line.

FIG. 6 is a panel of images showing O2KM cultured on Poly-D-Lysine+Laminin+MATRIGEL coated dishes +/−0.25 µM 5-Aza-Cytidine (5AC) for phenol-free self-renewal medium (SRM) under 5% $O_2$ for three days followed with or without 17-β Estradiol (E2) induction of the MyoDER fusion protein under 20% $O_2$ for two days in phenol red-free myogenic induction medium (MIM) supplemented with 3 µM CHIR99021. C. Phase-contrast images of O2KM on E2-induction day 2.

FIG. 7 shows Western blot analysis of MYOD1 (MyoD), MYF5 (Myf5), and MYOG (myogenin) in differentiated O2KM cell lysates harvested following indicated 2-day E2 induction regimens. MyoDER migration: ~75 kD. Expected endogenous MYOD1 migration: 45-50 kD.

FIG. 8 shows images of immunofluorescent detection of myocyte cell surface marker NCAM (Alexa568) and nuclei (DAPI) in S5AC-exposed O2KM cultures prior to, and following, a 2-day 10 µM E2 induction time-course.

FIG. 9 shows a panel of phase-contrast images of i. ground state undifferentiated O2K colonies cultured on Poly-D Lysine+Gelatin+Laminin under 5% $O_2$ in SRM, ii.-vi. adherent colonies differentiating from the ground state, as shown in panel i. for two days in differentiation medium (DM) under 20% $O_2$ supplemented with ii. 0 µM, iii. 1 µM, iv. 3 µM, v. 6 µM or vi. 9 µM CHIR99021. Non-adherent colonies were prevalent as embryoid bodies in cultures exposed to 6 µM (vii.) or 9 µM (viii.) CHIR99021.

FIG. 10. FIG. 10 shows a bar graph illustrating adherent O2K cell population change during differentiation. Percentages represent the ratio of adherent cells enumerated in cultures following two days in the presence of CHIR99021 at the concentrations indicated (shown in FIG. 9, panels ii.-vi.) relative to the adherent cells enumerated prior to differentiation from the ground-state (shown in FIG. 9, panel i.). n=3 for each enumerated culture condition.

FIG. 11 shows a bar graph of flow cytometric analysis of Annexin V labeled cells. Undifferentiated O2K colonies were cultured under 20% $O_2$ in differentiation medium the presence of 0, 1, 3 or 6 µM CHIR99021 for one day prior to analysis.

FIG. 12 shows Western Blot analysis of relative CTNNB1 (β-catenin) levels and phosphorylation (p-CTNNB1) at GSK3β substrates serine 33, 37 and threonine 41 in cultures differentiated from the ground-state (as shown in FIG. 9) in the presence of CHIR99021 at the concentrations indicated. Cultures were exposed to 50 nM Calyculin A and 30 µM MG-132 for 3 hours prior to harvest to stabilize detectable levels of p-CTNNB1 for comparative analysis.

Figure 20A:
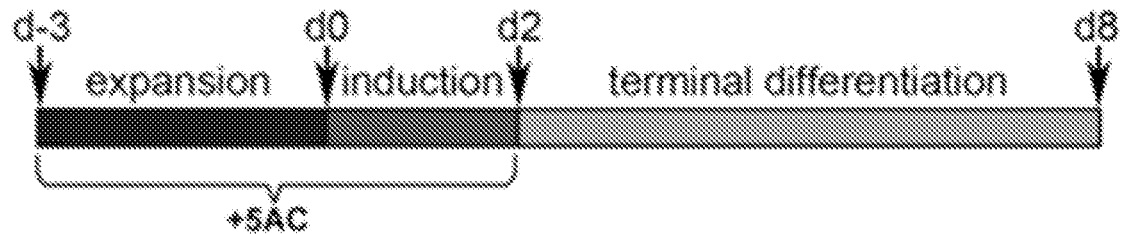
FIG. 20A is a schematic of the O2KM expansion and induction regimens, followed by the terminal differentiation regimen.
Figure 20B:
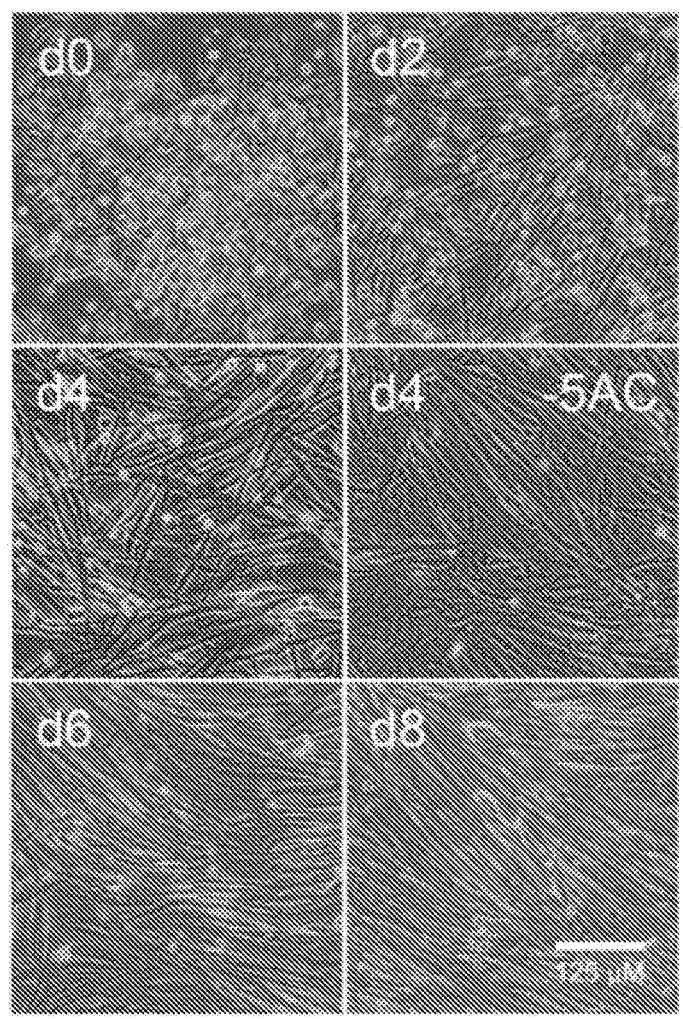
FIG. 20B shows myotube morphology and conformation. Post-induction (d2), piPSC developed as elongated, anisotropic, refractive myotubes when exposed to 5AC during the expansion and induction regimens.
Figure 20C:
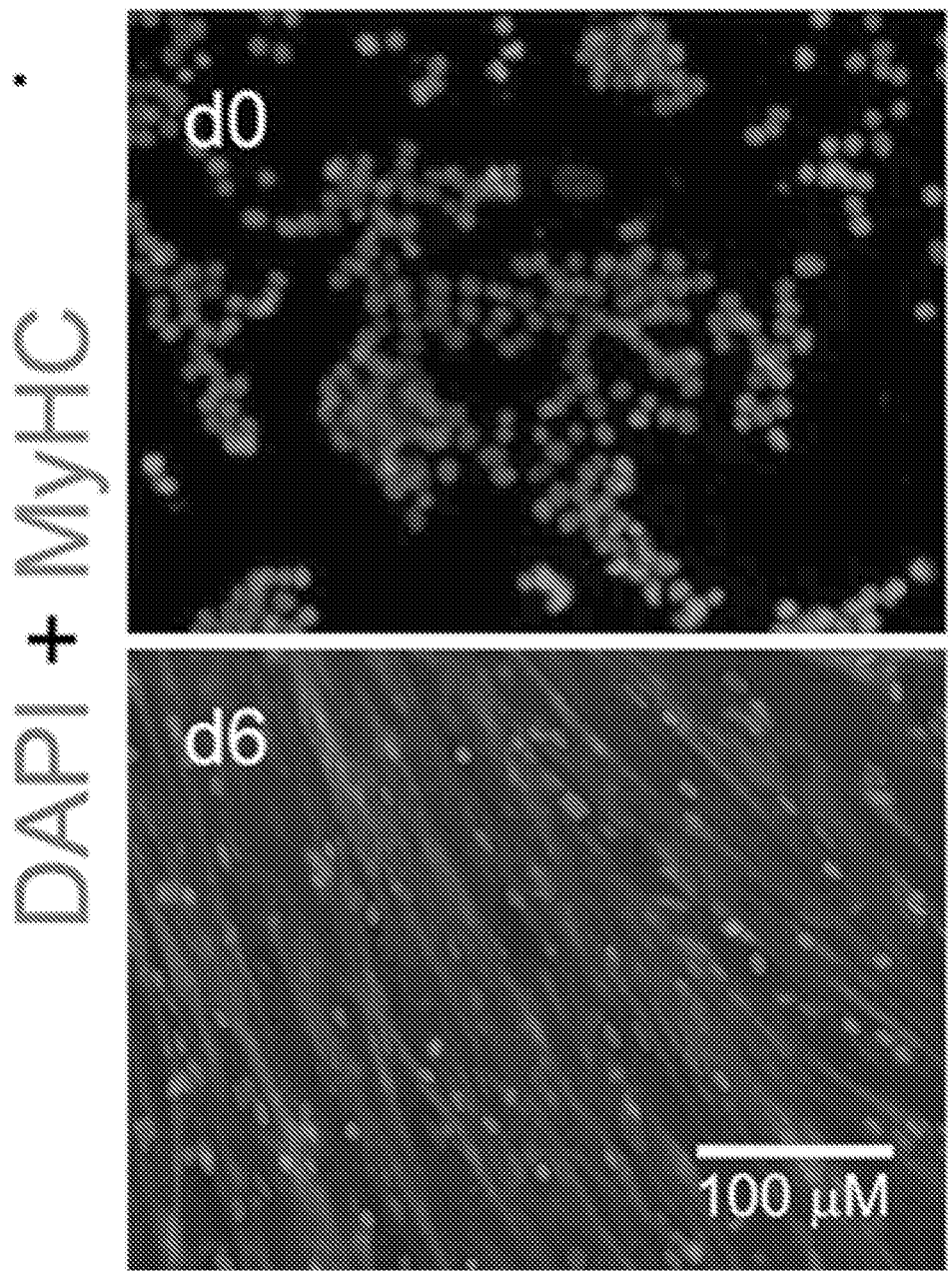
FIG. 20C shows uniform expression of myosin heavy chain by d6.
Figure 20D:
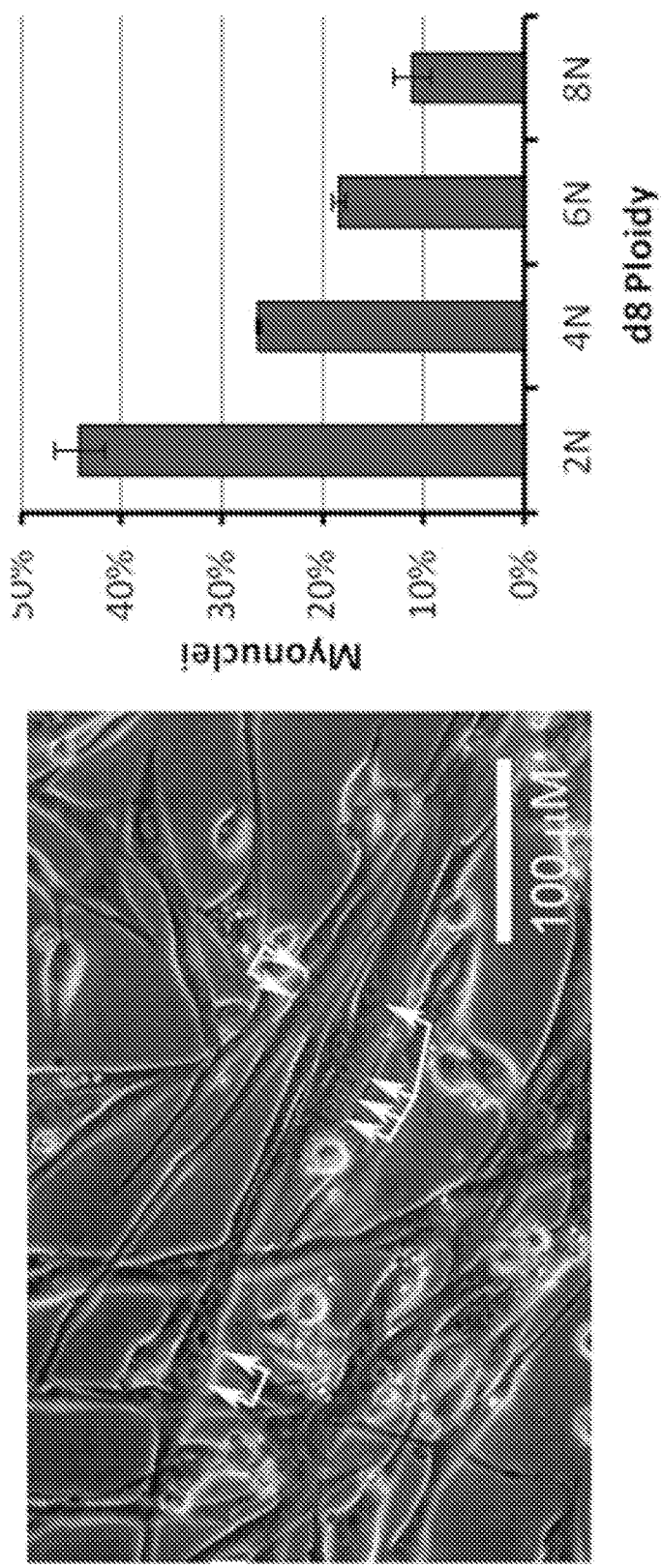

FIG. 20D shows myotube multinucleation. Left panel: enlarged image of d4 terminal differentiation cultures. Bracketed arrows indicate multiple nuclei within a single myotube. Right panel: myonuclei distribution by myotube ploidy by propidium iodide labeling and flow cytometry analysis. n=3 with standard deviation shown.

Figures 20E, 20F:
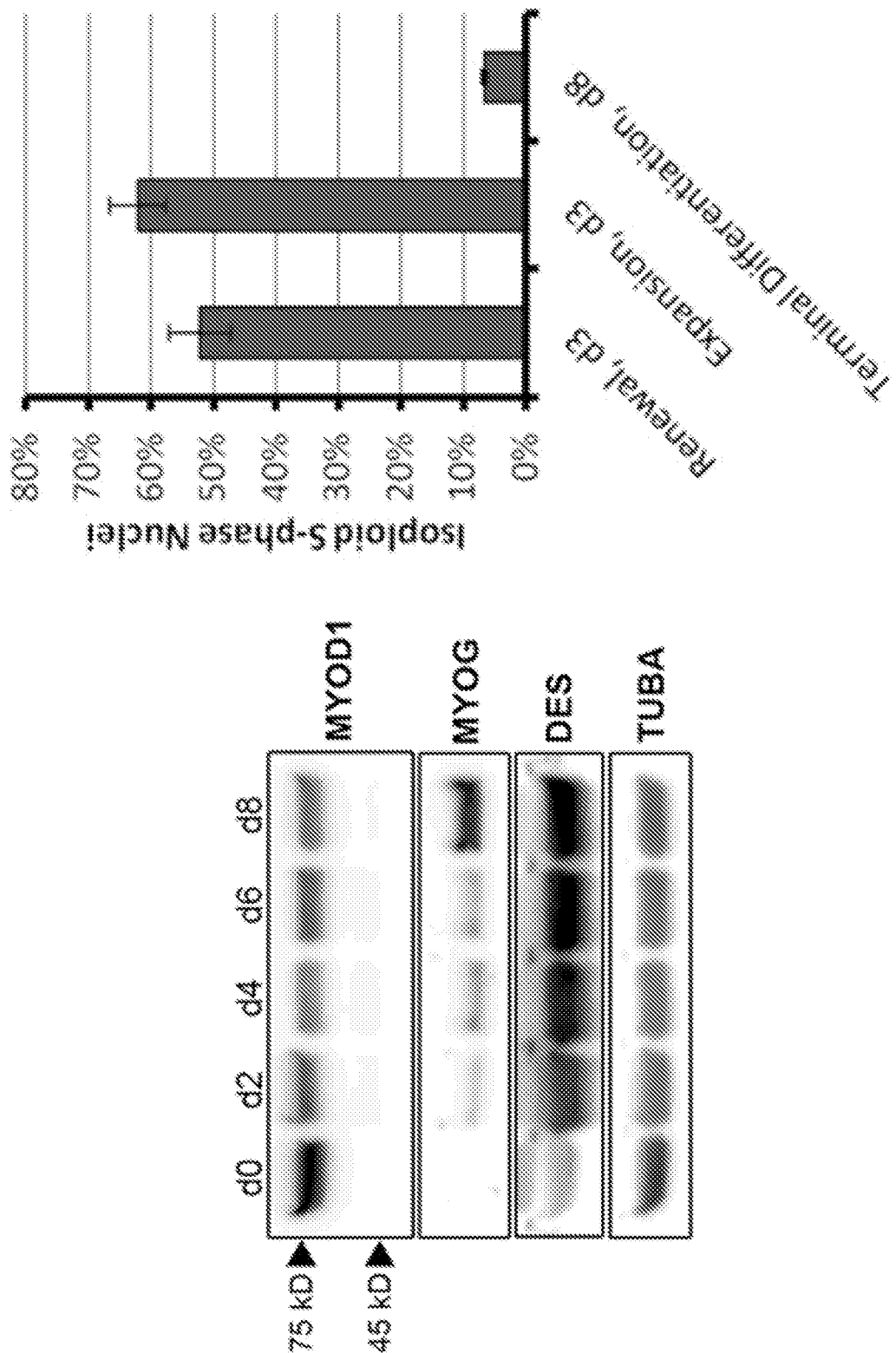

FIG. 20E Western blots show increasing expression of desmin (DES) and myogenin (MYOG) over the 8 d course.

FIG. 20F shows cell-cycle withdrawal concomitant with terminal differentiation.

Figure 20G:
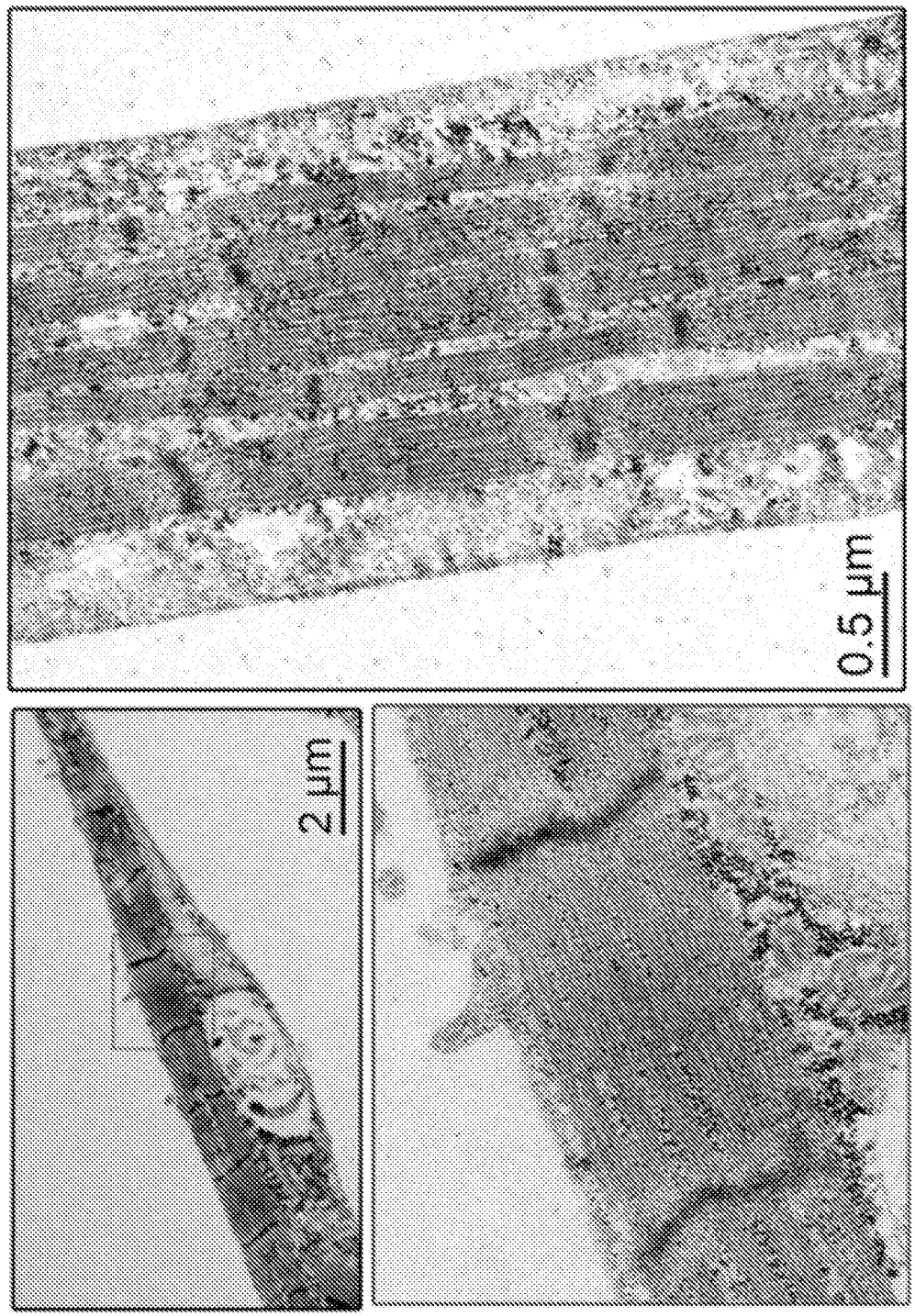

FIG. 20G shows Transmission Electron Microscopy of d6 myotubes. Sarcomeric structural units were aligned in single (left panels) and staggered, parallel rows (right panel).

Figure 21A:
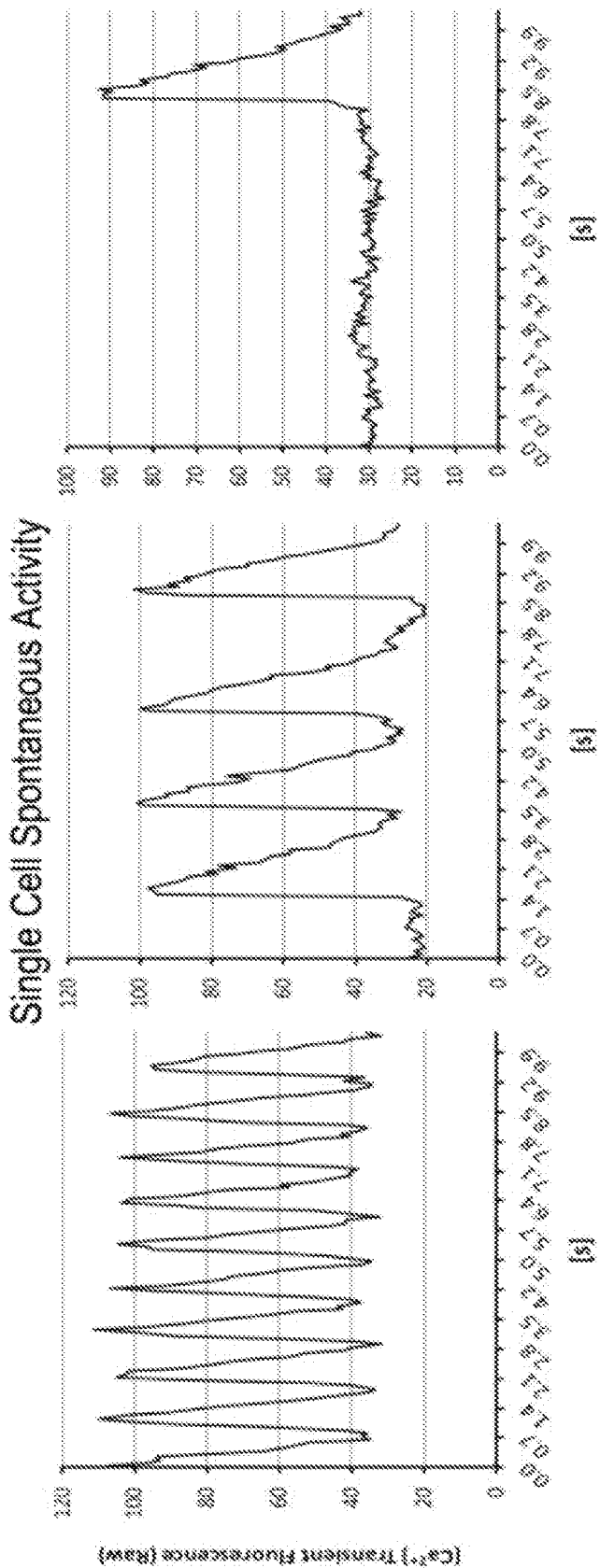

FIG. 21A shows asynchronous, single-cell transient cycles (left, middle and right panels) were observed in spontaneously contracting d6 myotube subpopulations.

Figure 21C:
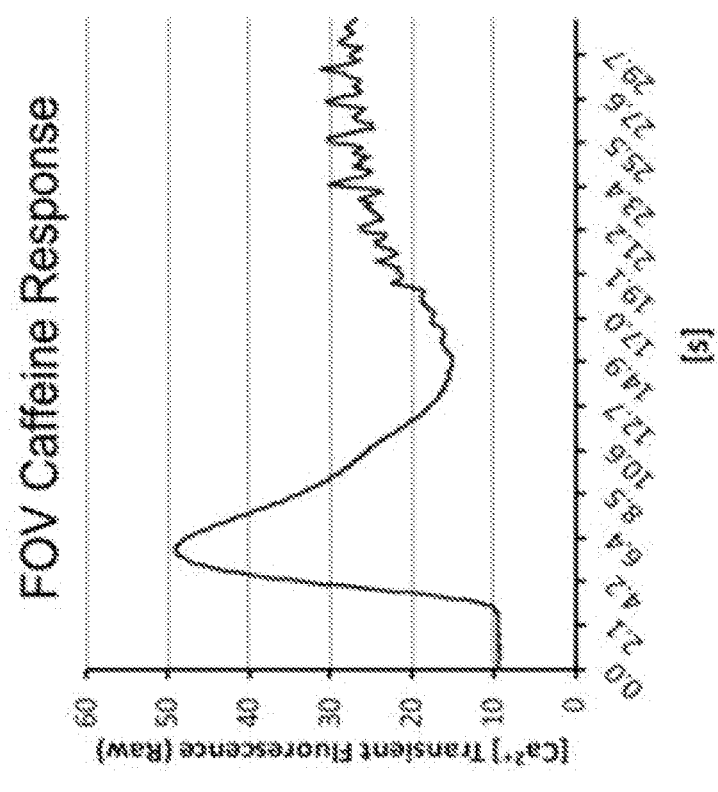
Figure 21B:
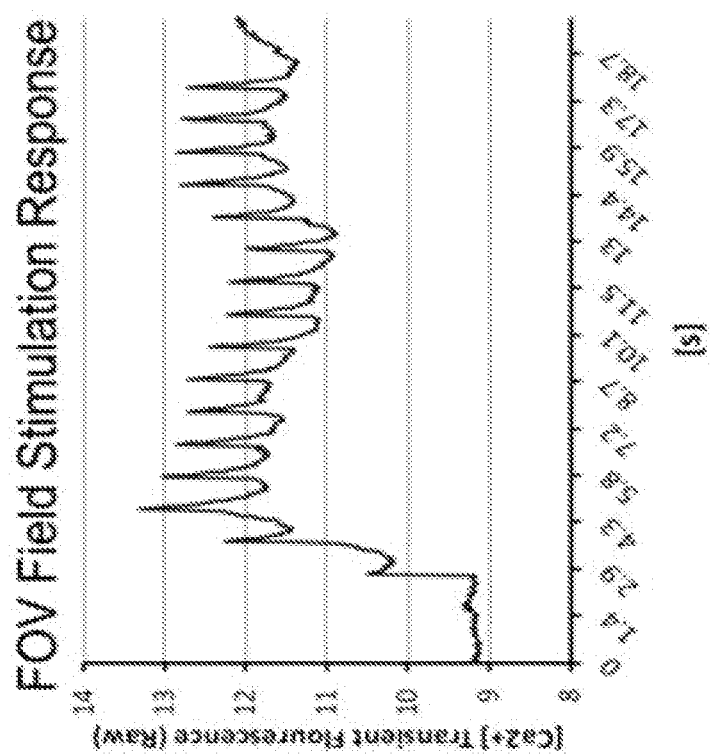

FIG. 21B shows FOV activation and synchronization of calcium transient cycles by 1.0 Hz field stimulation in d6 myotubes.

FIG. 21C shows FOV calcium transient activation of d6 myotubes by 10 mM caffeine.

Figure 21D:
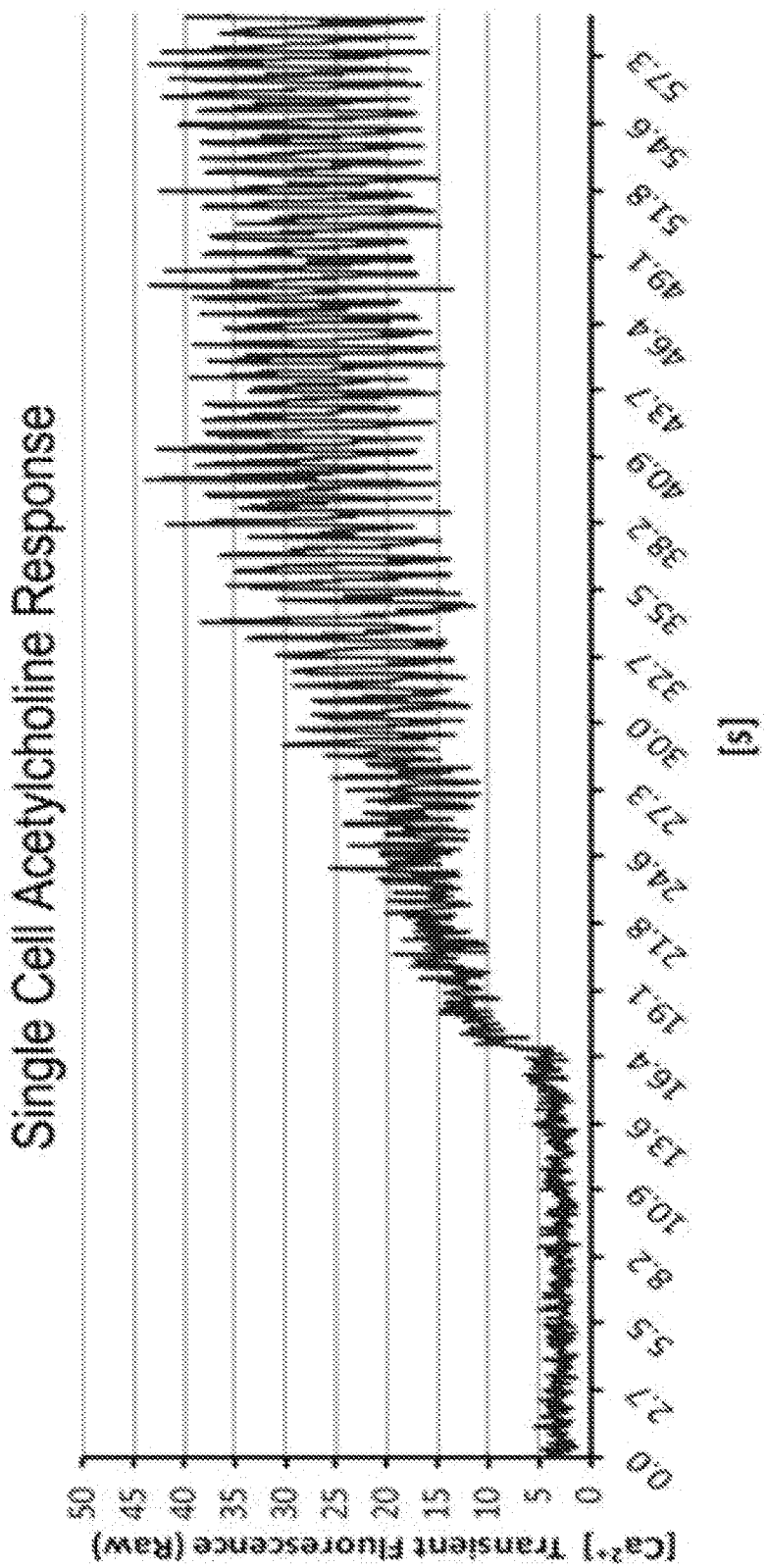

FIG. 21D: single-cell analysis of calcium transient activation in a d7 myotubes by 100 nM acetylcholine.

DETAILED DESCRIPTION

To the extent necessary to provide descriptive support, the subject matter and/or text of the appended claims is incorporated herein by reference in their entirety. It will be understood by all readers of this written description that the exemplary embodiments described and claimed herein may be suitably practiced in the absence of any recited feature, element or step that is, or is not, specifically disclosed herein.

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to whom this disclosure is directed. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, nucleic acid sequences are written 5' to 3' and amino acid sequences are written left to right in amino to carboxy orientation. The headings provided herein are not limitations of the various aspects of the disclosure, which can be had by reference to the specification as a whole.

All methods described herein can be performed in any suitable order unless otherwise indicated herein.

No language or terminology in this specification should be construed as indicating any non-claimed element as essential or critical.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value is intended to be included therein, and all smaller subranges are also included.

Provided herein are new and improved methods for generating functional skeletal muscle, for cultivating meat such as engineered tissue or other comestible product, from a cell source in vitro. Such methods are contemplated, for example, for livestock-autonomous meat production, wherein meat is any metazoan tissue or cell-derived comestible product intended for use as a comestible food or nutritional component by humans, companion animals, domesticated or captive animals whose carcasses are intended for comestible use, service animals, conserved animal species, animals used for experimental purposes, or cell cultures.

Also provided are in vitro-produced animal tissues, such as muscle tissue, made by any of the various aspects disclosed herein. In certain aspects, the cell source is a stem cell source, for example, a self-renewable stem cell line. Certain aspect of the methods employ a myogenic, inducible transgene-modified self-renewable cell line derived from an intended species. In certain aspects, the intended species can be any edible species including livestock and poultry species. In certain aspects, the intended species are livestock species such as domestic cattle, pigs, sheep, goats, camels, water buffalo, rabbits and the like. In certain aspects, the intended species are poultry species such as domestic chicken, turkeys, ducks, geese, pigeons and the like. In certain aspects, the intended species are common game species such as wild deer, gallinaceous fowl, waterfowl, hare and the like. In certain aspects, the intended species are aquatic species or semi-aquatic species harvested commercially from wild fisheries or aquaculture operations, or for sport, including certain fish, crustaceans, mollusks, cephalopods, cetaceans, crocodilians, turtles, frogs and the like. In certain aspects, the intended species are exotic, conserved or extinct animal species. In certain aspects, the intended species are any metazoan species demonstrating the capacity for skeletal muscle tissue specification. In certain aspects, the intended species are for research or for therapeutic purposes, such as humans, primates, rodents including rats and mice, and companion animals such as dogs, cats, horses, and the like.

In certain aspects, the cell line is regulated by a double-switch mechanism to either maintain the cell line in self-renewal process or direct myogenic differentiation.

A parent/host cell line of aspects disclosed herein has the properties of being immortal (self-renewing) and having the potential to differentiate, reprogram, specify or otherwise convert to skeletal muscle lineage, such as following regimens comprising one or more components that direct myogenic conversion. Three classes of stem cell may be employed as cell sources for scalable cultivation: (1) lineage-restricted primary adult progenitor stem cell isolations, (2) lineage-restricted immortalized cell lines, and (3) pluripotent stem cells lines. It has been determined that each of these approaches has advantages and disadvantages in serving as a cell source for cultured meat production.

Lineage-Restricted Primary Adult Progenitor Stem Cell Isolations. These include adult progenitor cells committed to lineages constituting meat products such as skeletal muscle. Skeletal muscle progenitor cells include, but are not limited, to satellite cells, myoblasts and myocytes. Their advantages include: i) primary adult progenitor cells are restricted to specific lineages and require little or no in vitro specification to desired lineages; and ii) primary adult progenitor cells do not require genetic modification for lineage specification. Their disadvantages include: i) they must either be harvested from a freshly slaughtered animal carcass or procured from an invasive biopsy. Either method conveys dependence on livestock and compromises the benefit of livestock-autonomous production to the extent that livestock are used in the process; ii) primary cell isolation is a highly inefficient process. The desired cells comprise a fraction of the source tissue. A subfraction of the desired cells survive the isolation process. Desired cell lineages must be isolated from mixed populations of surviving cells, requiring additional purification and expansion steps; iii) primary adult progenitor cells are subject to the 'Hayflick Limit', wherein cells can divide only limited number of times before they lose their capacity to proliferate. Moreover, primary adult progenitor cells lose their ability to terminally differentiate in a manner concordant with extended passage. Thus, additional cells must be procured from primary cell isolations, thereby limiting cultivation scalability from a single isolation; and iv) primary cell culture of lineages of tissues applicable to cultured meat production, such as skeletal muscle, are anchorage dependent-limiting methods for volumetric scalability of cultures. In suspension culture, these cells may be susceptible to cell death by anoikis.

Lineage-Restricted Immortalized Cell Lines. These are lineage-committed primary cells that are genetically altered to self-renew indefinitely while retaining their capacity to terminally differentiate or lineage-restricted. Their advantages include: i) "perpetually self-renewing" (i.e. not subject to the 'Hayflick Limit') and can expand indefinitely for scalable and livestock-autonomous cultivation; ii) restricted to specific lineages and require little or no further in vitro specification. Their disadvantages include: i) immortalized, lineage-restricted cell lines from certain species with the capacity to differentiate along lineages applicable to cultured meat production (e.g. skeletal muscle) may require development; ii) cultures of lineage-committed cell lines are anchorage dependent, limiting scalability. In suspension culture, lineage-committed cell lines may be susceptible to cell death by anoikis; and iii) cellular transformation(s) enabling 'immortalization' necessitates genetic modification. The necessary genetic modifications that immortalize applicable primary cell populations without interfering with their capacity to terminally differentiate are not well characterized.

Pluripotent Stem Cells Lines: Pluripotent stem cell lines include embryonic stem cells or induced pluripotent stem cells (iPSC) that maintain the capacity to self-renew in the undifferentiated state, or alternately differentiate to any tissue lineage. Their advantages include: i) in general, pluripotent stem cell lines proliferate at a higher rate than primary or immortalized lineage-restricted cell lines, reducing the time required for biomass expansion in production processes; ii) pluripotent stem cells may be cultivated as embryoid bodies in suspension culture, thereby enhancing culture scalability per unit of culture volume. Moreover, embryoid bodies may be cultured as 'bio-ink' compatible with micromold and bioprinting tissue assembly methods; and iii) like immortalized lineage-restricted cell lines, pluripotent stem cells are not subject to the 'Hayflick Limit' and can expand indefinitely for scalable, livestock-autonomous cultivation. Their disadvantages include: i) authentic embryonic stem cell lines derived from certain species may require development; ii) methods for reprogramming and self-renewal of iPSC may be transgene-dependent. Hence, iPSC pluripotency may require genetic modification for induction and self-renewal of the undifferentiated state. Efficient iPSC differentiation requires mechanisms for silencing the transgenes used for reprogramming and maintenance of the undifferentiated state mutually exclusive to the differentiated state to avoid conflicting transcription network activation disadvantageous to desired lineage specification; and iii) relative to lineage-restricted primary adult progenitor stem cells and immortalized cell lines, pluripotent stem cells, in general, require additional lineage specification steps to develop and enrich the desired lineage specification.

Other parental/host cells lines in addition to the three stem cell classifications provided above are also contemplated herein. For example, induced trophoblast cell lines (representing non-pluripotent, non-somatic immortalized cells of extra-embryonic type), whose myogenic potential was established previously by the teratoma assay, may be suitable for myogenic conversion as well. For example, somatic cell lines partially reprogrammed to pluripotency may possess myogenic potential but fail to form teratomas representing three embryonic germ layers. For example, though their existence is controversial, STAP cell lines (stimulus-triggered acquisition of pluripotency) may be myo-potent and self-renewing.

O2K cell line. The O2K cell line is an induced pluripotent stem cell line established from the inner cell mass of a pre-implantation porcine embryo. The O2K cell line has been studied and it was discovered that the self-renewal state of O2K can be maintained by transcriptional activation of POU5F1 and KLF4 transgenes by doxycycline (i.e. DOX) using a 'Tet-On' induction system.

Figure 1:
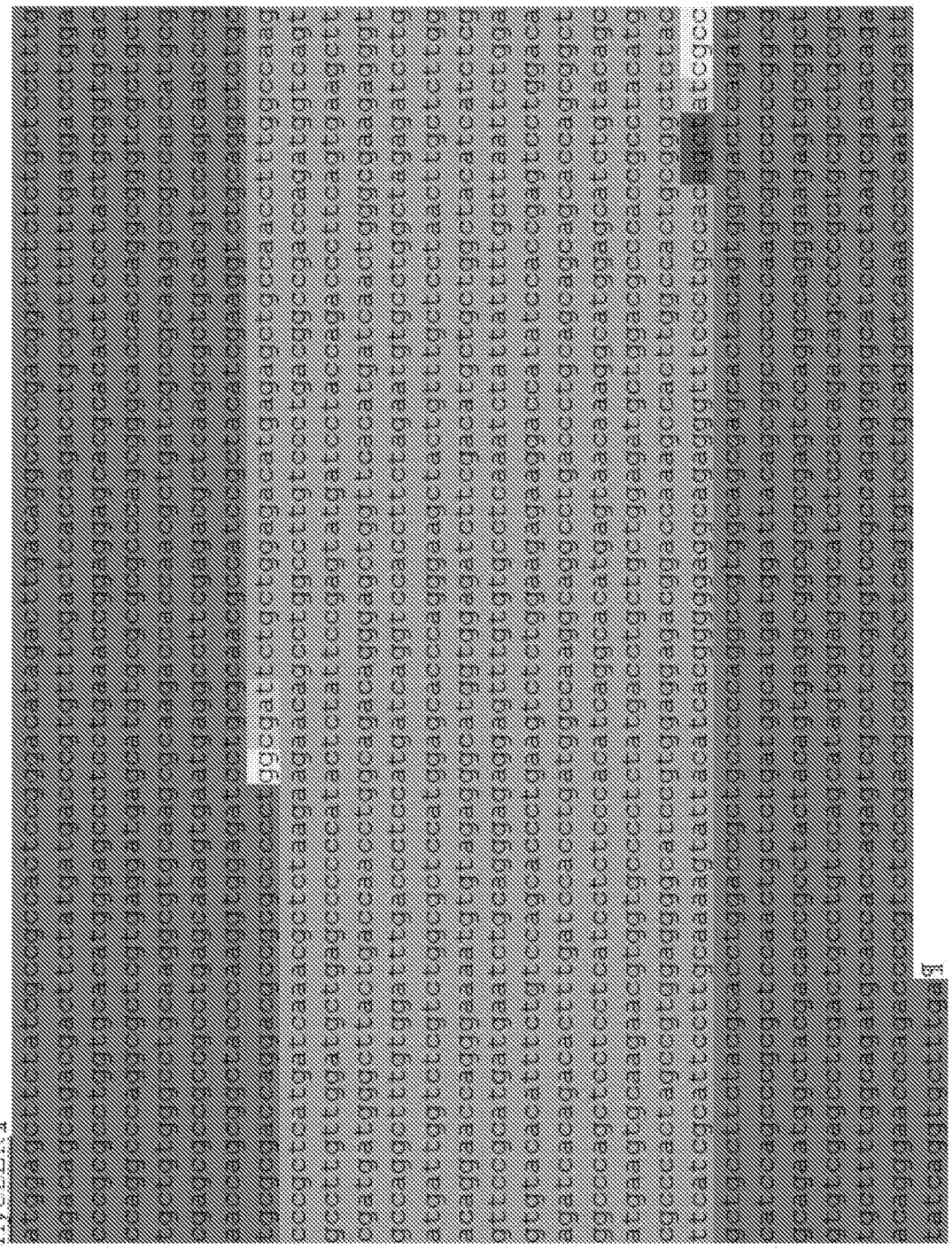

MYOD1 transcription factor. MYOD1 (i.e. MyoD) is a dominant regulator of skeletal muscle lineage commitment. The MyoDER construct has been described previously, consisting of a genetic fusion of the murine MYOD1 gene and the sequence encoding the ligand binding domain of the human estrogen receptor α, shown in FIG. 1 (SEQ ID NO: 1). In FIG. 1, the MyoDER consists of a genetic fusion between the murine MYOD1 gene at the Nar I restriction endonuclease digest site with the ligand binding domain coding sequence of the ESR1 (i.e. human estrogen receptor α) nucleotides 844-1781. Non-specified and Cla 1 linker sequences are also present. The myogenic specification activity of the MyoDER fusion construct is post-translationally induced by addition of the estrogen receptor α ligand, 17β-Estradiol (i.e., E2). In the absence of the 17β-estradiol, MyoDER remains in an inactive state. The MyoDER construct is herein referred to as "inducible MyoD."

Figure 2:
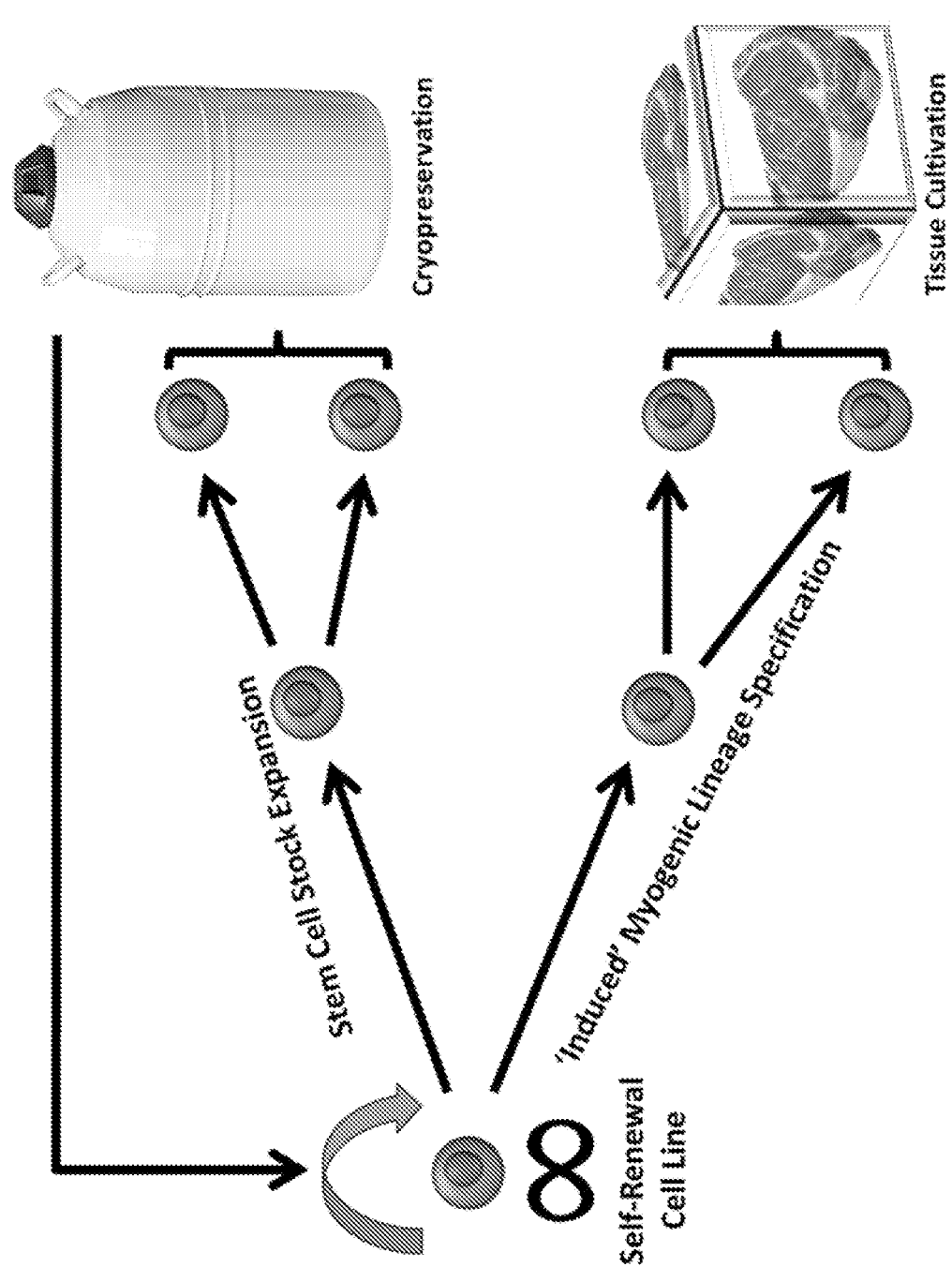

Referring now to FIG. 2, one aspect is cell-stock-expansion, i.e., expansion of the cell line in self-renewal conditions necessary for the maintenance of cell stocks for continued scalable cultivation. Another aspect is the lineage-specification/differentiation, i.e., inducing myogenic lineage differentiation for further tissue cultivation process. Thus, certain aspects may be summarized as comprising two main steps: i) modifying a selected self-renewing cell line with a myogenic transcription factor to produce an myogenic-transcription-factor-modified cell line, and ii) inducing such modified cell line by exogenous regulation to maintain in self-renewal process or advance to differentiation process. As used herein, "modifying" a cell line with an myogenic transcription factor refers to inserting a nucleic acid vector or construct operably encoding a myogenic transcription factor (such as by transfection, transduction, transformation, and the like) into the cell line, wherein the modified cell line expresses the myogenic transcription factor. In certain aspects, the inserted myogenic transcription factor is inducibly-expressed to produce an inducible-myogenic transcription factor cell modified cell line. As used herein, "inducibly," "inducible," and the like refers to any genetically engineered approaches that may be used to exogenously regulate the activities of a gene product such as a myogenic transcription factor. Inducible approaches include, but are not limited to, regulation of myogenic transcription factor activity by ligand inducible transcription factor technology (e.g., tet-on, tet-off, RheoSwitch), site-directed recombination technology (e.g., Cre-LoxP, flp-FRT), transposon technology (e.g. Sleeping Beauty, PiggyBac), ligand binding receptor fusion technology (e.g., estrogen, progesterone, androgen, thyroid hormone, glucocorticoid hormone, tamoxifen ligand agonists), and transient transfection of extrachromosomal expression vectors bearing a myogenic transcription factor gene. In certain aspects, the nucleic acid construct or vector is chromosomally integrated into the modified cell line. Representative examples of self-renewing cell lines include those selected from a group consisting of embryonic stem cells, induced pluripotent stem cells, and immortal lineage-restricted cell lines. In certain aspects, such self-renewing cell lines are derived from species intended for dietary consumption or for research or for therapeutic purposes. Representative examples of myogenic transcription factors include, used alone or in combination, MYOD1, MYOG, MYF5, MYF6, PAX3, PAX7, paralogs, orthologs, genetic variants thereof, or transcriptional activation agonists of the respective promoter recognition DNA sequences of the myogenic transcription factors disclosed herein.

Figure 3:
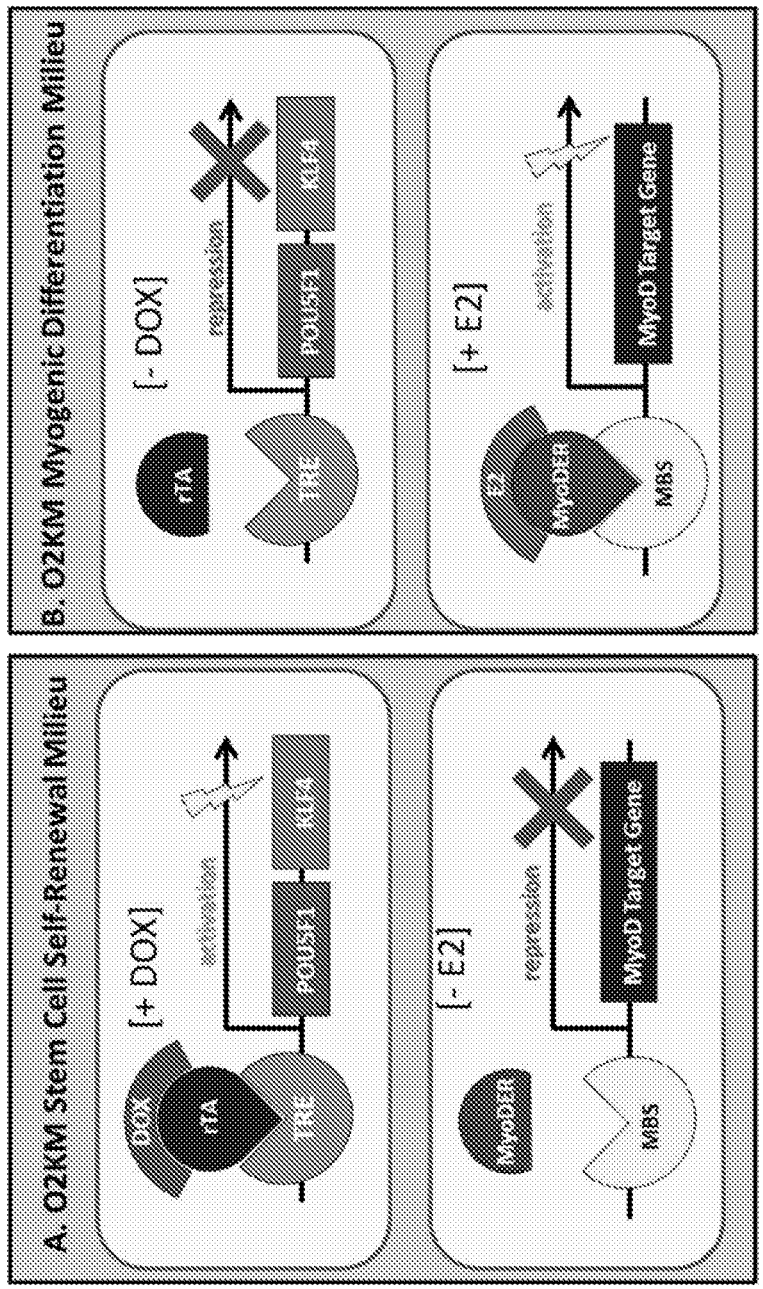

Reference is made now to FIG. 3, which includes exemplary schematic illustrations of the double-switch mechanism of the myogenic modified O2KM cell line regulated by DOX or E2. As shown in FIG. 3, during the O2KM stem cell self-renewal process, the expression of the pluripotency transgenes POU5F1 and KLF4 is induced in the presence of DOX in the self-renewal medium (SRM), while such expression is repressed when DOX is absent. Similarly, during the O2KM myogenic differentiation process, myogenic differentiation is activated by the inducible MyoD transgene in the presence of E2 in the myogenic induction medium (MIM), while such directed differentiation is inactive when E2 is absent.

Certain aspects provide differentiation/specification methods comprising additional reagents other than E2 in the MIM to prevent cell death and to modulate the epigenetic state of chromatin. For example, a Glyogen Synthase Kinase-3β (GSK3β) inhibitor can be added to the SRM and MIM to activate the canonical WNT signaling pathway, in turn, enhance myogenic differentiation and reduce cell death at the time of DOX withdrawal. Without being limited by theory, in certain aspects, the epigenetic modular alters the chromatin activation by myogenic transcription factors and/or enhances expression of myogenic transcription factors, such as MYF5.

It is understood that GSK3β inhibition includes targeting with small-molecules. Gene editing is also a promising approach to enhance skeletal muscle specification by WNT signaling activation. For example, GSK3β may be inhibited in the host/parental cell line by mutating the GSK3β alleles either by sequence-specific insertion or deletion technology (i.e. Zinc-Finger Nuclease, TALEN, CRISPR). Mutating the endogenous promotor region can be used to repress expression of GSK3β. Alternately, the GSK3β open reading frame may be deleted or mutated using the same methods to abolish GSK3β activity. Likewise, the downstream phosphorylation target of GSK3β, beta-catenin (CTNNB1) may be mutated at the codons coding for residues phosphorylated by GSK3β, thereby preventing phosphorylation of CTNNB1 by GSK3β, resulting in a constitutively active, stable CTNNB1. Such "gene-editing" methods would reduce the cost of GSK3β inhibition by small-molecule targeting and potentially improve the safety profile of the meat product, as additional chemicals would not be required to inhibit GSK3β during the process. It is contemplated that a third approach to Wnt-signaling inhibition includes the use of anti-sense nucleic acid inhibitors to GSK3β or other factors antagonistic to the WNT pathway. These may include RNA interference methods using sequence-targeting shRNA or miRNA.

Certain specific aspects provide for use of a GSK3(3 inhibitor to promote cell survival, for example at the time of DOX withdrawal. One illustrative example of a GSK3β inhibitor is CHIR99021. Additional representative GSK3β inhibitors may include, without limitation: lithium chloride, 6-bromoindirubin-3'-oxime (BIO), SB216763, CHIR-98014, TWS119, Tideglusib, IM-12, 1-Azakenpaullone, AR-A014418, and SB415286. Without being bound by theory, it is believed that concomitant with DOX, both self-renewal of undifferentiated cells is maintained by a WNT signaling pathway involving the inhibition of GSK3β.

Without being bound by theory or limited by any specific representative example, it was observed that simultaneous withdrawal of both DOX and the GSK3β inhibitor CHIR99021 from the culture medium supplemented with N-2 and B-27 serum replacements precipitates massive cell death of differentiating O2K parental line within 48 h hours. Withdrawal of DOX in the presence of CHIR99021 enabled survival of the differentiating O2K. Death by differentiating O2K cells in the absence of a GSK3β inhibitor and reciprocal survival in the presence thereof was confirmed by morphology, cell adhesion assay, cleaved caspase-3 accumulation, and Annexin V labeling. In the parental O2K cell line, inhibition of GSK3β concordantly resulted in the stabilization and activation of its phosphorylation substrate, CTNNB1, the downstream positive effector of the canonical WNT signaling pathway. WNT signaling plays crucial roles in both mesoderm specification from the undifferentiated ground-state pluripotency, pre-myogenic enrichment from unpatterned mesoderm and terminal differentiation of committed myocytes both in vivo and in vitro. In agreement, extended culture of the O2K line in the absence of DOX, and in the presence of a GSK3β inhibitor, supported differentiation toward the pre-myogenic paraxial mesoderm, as evidenced by the expression of PAX3 and concomitant loss of POU5F1 and KLF4 expression. Furthermore, in combination with 5AC, the GSK3β inhibitor enhanced expression of the myogenic transcription factor MYF5 in differentiating O2K. Moreover, a GSK3β inhibitor, such as CHIR99021, enhanced the terminal differentiation of the myogenic murine C2C12 cell line into multi-nucleated myotubes, as shown in Table 1.

Table 1 lists the influences of extracellular matrix effectors (i.e. Gelatin, Poly-D-Lysine, Laminin, MATRIGEL) and soluble factors (E2, CHIR99021) on the terminal differentiation of the murine C2C12 myoblast by assessment of the size and extent of myotube formation proceeding a 5-day differentiation time course. (Cultures were scored from [*****], indicating robust myotube formation to [−] indicating non-detectable myotube formation.)

TABLE 1

Influence of Extracellular Matrix effectors and Soluble factors on the terminal differentiation.

| | Basal Medium | +5 µM E2 | +3 µM CHIR | +5 µM E2, +3 µM CHIR |
|---|---|---|---|---|
| Gelatin | *** | ** | *** | ** |
| Gelatin + Poly-D Lysine | *** | * | * | — |
| Laminin + MATRIGEL + Poly-D Lysine | *** | * | ** | ** |
| Laminin + MATRIGEL | *** | * | **** | ** |
| Laminin | *** | * | *** | * |
| MATRIGEL | *** | ** | ***** | *** |

In certain aspects due to its multifunction: (1) suppressing cell death following DOX withdraw, (2) supporting differentiation toward the pre-myogenic state, (3) enhancing myogenic specification, and (4) enhancing terminal differentiation, a GSK3β inhibitor when retained in the culture medium during differentiation (in the absence of DOX), is deemed compatible with the inducible myogenic transcription factor directed lineage specification and subsequent terminal differentiation conditions by derivative myocytes. For example, CHIR99021 was retained in the O2KM cultures following DOX withdrawal during subsequent E2-induced lineage-specification and terminal differentiation processes.

However, though the aforementioned GSK3β inhibitor-supplemented culture regimen supported cell survival and myogenic lineage specification by O2KM to differentiated cells with distinctive myocyte-like spindle morphology, the derivative cells failed to terminally differentiate into refractive elongated myotubes. Therefore, a epigenetic modulator was used to enhance the expression of myogenic genes in cells otherwise non-permissive to myogenesis and enhance terminal differentiation of lineage committed myoctes to mature myofibers. To enable terminal differentiation of O2KM, cells were cultured in the presence of 5-Aza-Cytidine (5AC) for 72 hours preceding DOX withdrawal, for 48 hours during E2 induction, followed by a terminal differentiation period up to 6 additional days. In O2KM derived myocytes cultured in the presence of 5AC, MYF5 expression was enhanced and cells exhibited a refractive myofibril morphology, whereas myocytes derived in the absence of 5AC expressed reduced MYF5 and exhibited an flattened morphology atypical to mature myofibrils. This distinction may explained by the enhanced expression of the myogenic transcription factor MYF5 observed only in the 5AC-exposed O2KM prior to and following 48 hours of DOX withdrawal In conjunction with enrichment of the lower molecular weight, non-phosphorylated myogenin isoform, known to be the active transactivator, the morphological distinction among these cultures may be explained by MYF5 expression enhanced by 5AC exposure. It is understood that epigenetic modulation entails alteration of chromatin structure influencing transcription factor binding and targeted transcriptional activation by altering the DNA methylation patterns and post-translational modification of nucleosome-associated histones. It is understood that epigenetic modulation may entail small-molecule agonists or antagonists targeting epigenetic pathways or expressed proteins comprising epigenetic machinery. One illustrative example of a small-molecule epigenetic modulator is 5-Aza-Cytidine (5AC). Additional representative examples of small molecule epigenetic modulators include 5-Aza-2'-deoxycytidine, RG108, Scriptaid, sodium butyrate, trichostatin A, Suberoylanilide Hydroxamic Acid, MS-275, CI-994, BML-210, M344, MGCD0103, PXD101, LBH-589, Tubastatin A, NSC3825, NCH-51, NSC-3852, HNHA, BML-281, CBHA, Salermide, Pimelic Diphenylamide, ITF-2357, PCI-24781, APHA Compound 8, Droxinostat, and SB-939. Representative examples of proteins involved in epigenetic modulation include histone deacetylase paralogs, histone acetyltransferase paralogs, tet-methycytosine dioxygenase paralogs, histone demethylase paralogs, histone methyltransferase paralogs, and DNA methyltransferase paralogs, histones, and subunits of chromatin remodeling complexes including Mi-2/NuRD (and its components such as methyl-CpG-binding domain protein 3 (MBD2)) and SWI/SNF (and its components such as BAF60 and BAF60C). It is further understood that respective activities of protein epigenetic modulators may be influenced by representative modalities such as targeting by small-molecule factors, over-expression of a respective exogenous transcript, anti-sense RNA-targeted respective transcript degradation, RNAi, and targeted mutation at the genetic locus.

The following disclosed embodiments are merely representative. Thus, specific structural, functional, and procedural details disclosed in the following examples are not to be interpreted as limiting.

EXAMPLES

Methods

O2KM cell line. The O2KM cell line was derived from the parental O2K cell line by lentiviral insertion of a blasticidin-selectable transgene cassette containing the MyoDER open reading frame sequence (ORF). As referred to in this example section, O2K cells/cell line and piPSC cells are used interchangeably. The lentiviral vector, illustrated in FIG. 4A, was prepared by cloning the MyoDER ORF (Addgene #13494) downstream of the CMV promoter of the pLentiCMVBlast destination vector (Addgene #17451) between the attR1 and attR2 recombination sites from an pENTR/D-TOPO entry vector (Life Technologies #K2435-20) clone containing the PCR-amplified MyoDER ORF. To prepare the lentiviral supernatant, 293FT cells were co-transfected with the prepared pLentiCMVBlast[MyoDER] plasmid, the pMD2.G envelope plasmid (Addgene #12259) and the psPAX2 packaging plasmid (Addgene #12260) using the PolyJet transfection reagent (Signagen

SL100688). O2K was transduced with pseudovirus concentrated from the 293FT supernatant. Transduced O2K were cultured in phenol-red free culture medium and selected four days with 10 µg/mL blasticidin followed by two additional days with 15 µg/mL blasticidin. Selected cells were designated as O2KM. Expression of MyoDER in the O2KM stock was verified by Western blot, FIG. 4B

Figure 5:
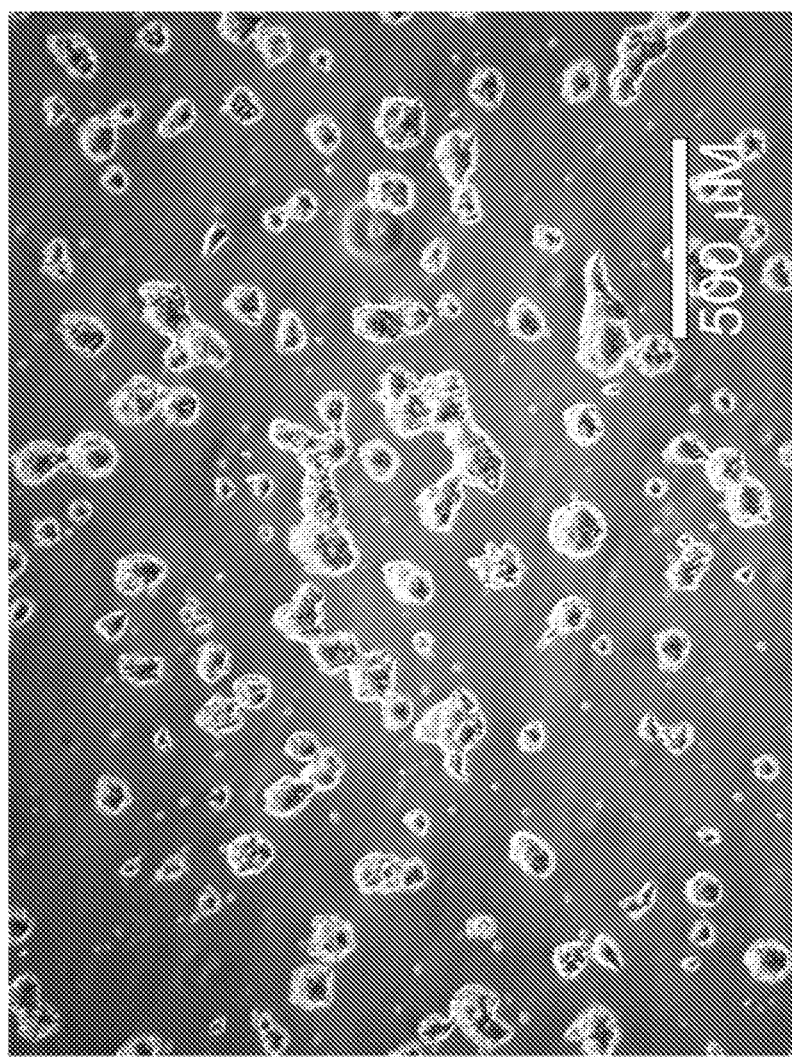

O2KM stem cell stock expansion in presence of DOX. O2KM stem cell renewal milieu was conducted as for the parental O2K line, with the following exception: phenol-red free formulations of DMEM/F-12 and neurobasal medium were substituted for the phenol-red containing formulations to avert pleotropic agonistic effects on MyoDER (i.e. activation). The O2KM cell stock self-renewal medium (SRM) consisted of the following components: phenol-red-free neurobasal medium (Life Technologies #12348-017), phenol-red free DMEM-F12 (Life Technologies #11039-021), 1× non-essential amino acids (Sigma-Aldrich #M7145), 0.5× Glutamax (Life Technologies #35050061), 0.000007% β-Mercaptoethanol, 0.5× N2 Supplement (Life Technologies #17502048), 0.5× B27 Supplement Minus Vitamin A (Life Technologies #12587010), 0.1 mg/mL Bovine Serum Albumin, 2 µg/mL doxacycline hyclate (i.e. DOX), 10 ng/mL human leukemia inhibitory factor (hLIF, Millipore #LIF1050), 3 µM CHIR99021, 0.8 µM PD032591 and 0.1 µM PD173074. Herein forth, the three inhibitors CHIR99021, PD032591 and PD173074 are collectively regarded as '3i'. Alternatively, N-2 and B-27 serum replacements were substituted using 15% KnockOut Serum Replecement (KOSR; Life Technologies #A15870). O2KM maintained by enzymatic dissociation of colonies and passages of cells onto culture dishes coated with poly-D lysine and murine laminin in phenol-free SRM under 5% $O_2$ every 3 d. In these self-renewal conditions, O2KM maintained compact, stem cell-like morphology as the parental O2K line, as shown in FIG. 5.

Figure 9:
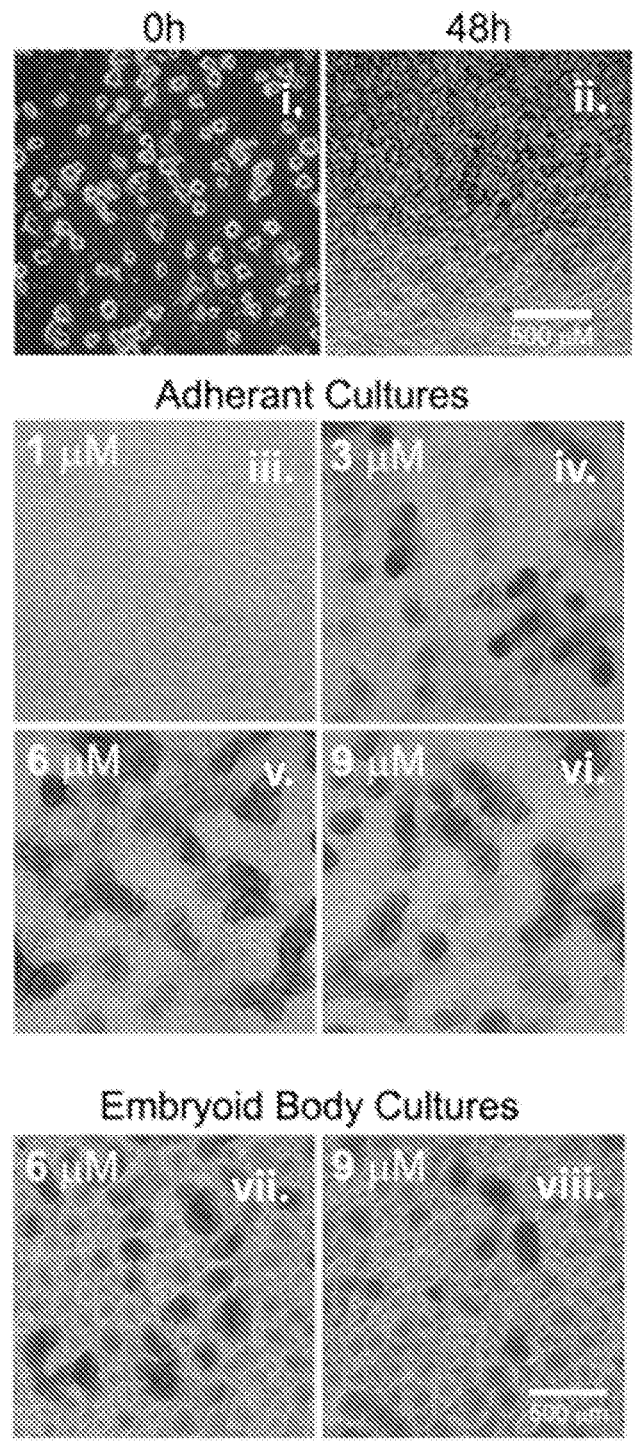
Figure 10:
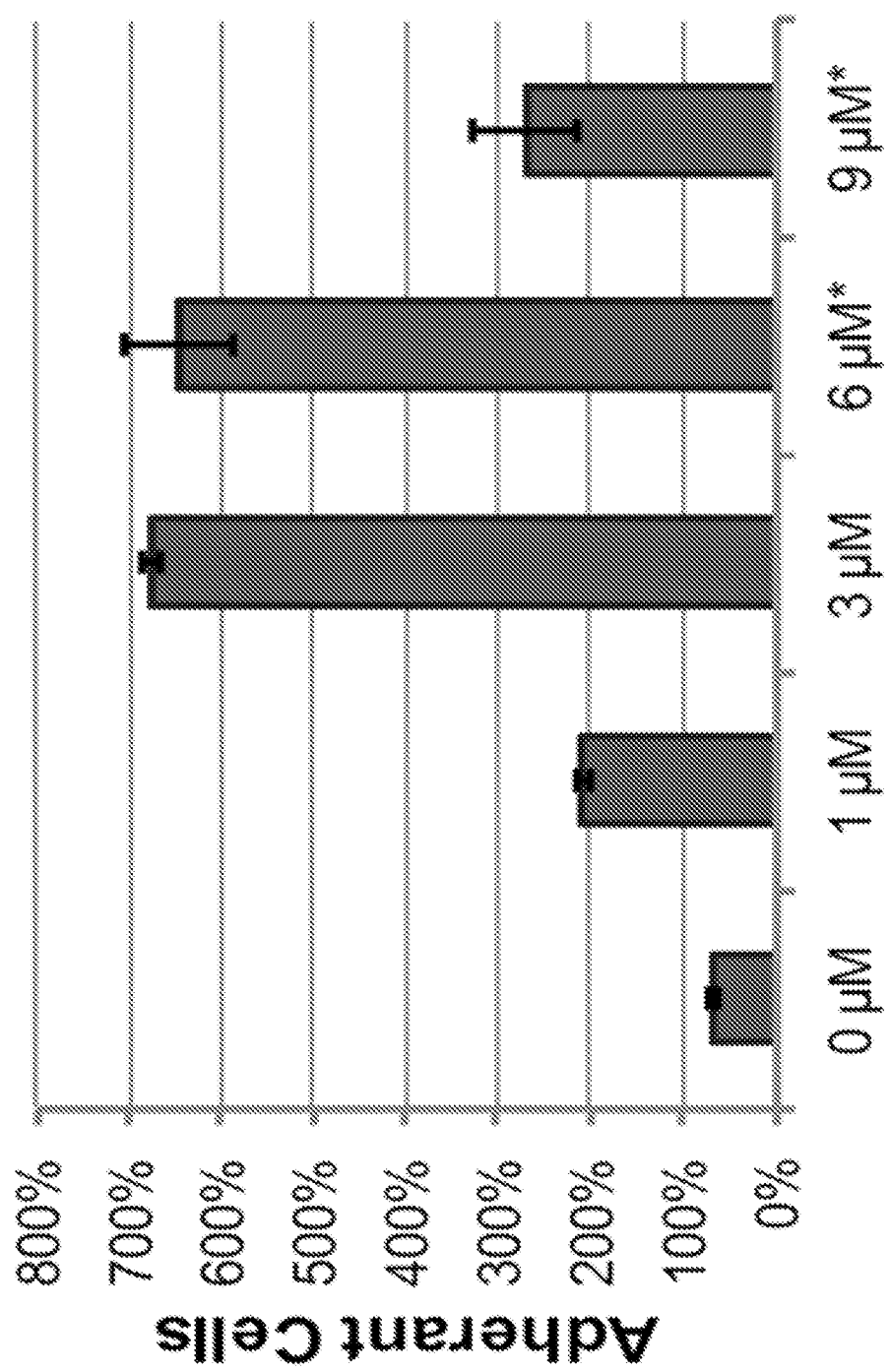
Figure 11:
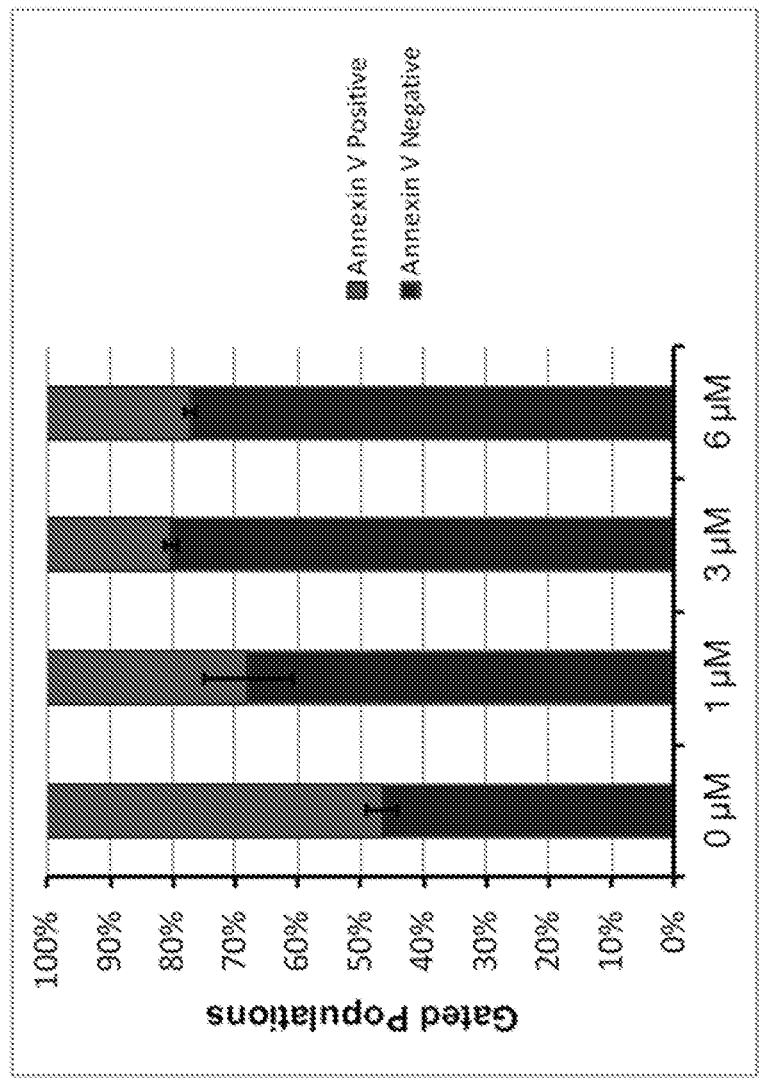
Figure 12:
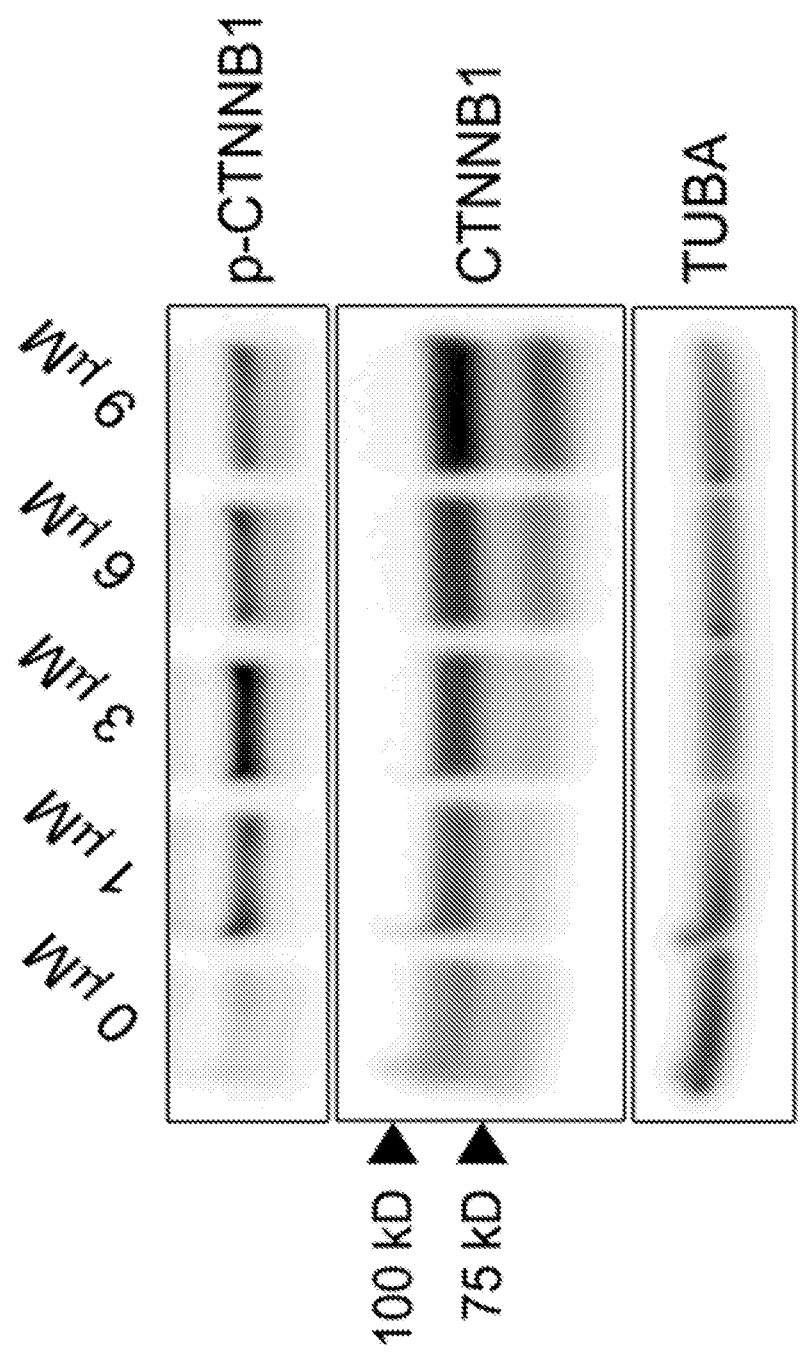
Figure 13A:
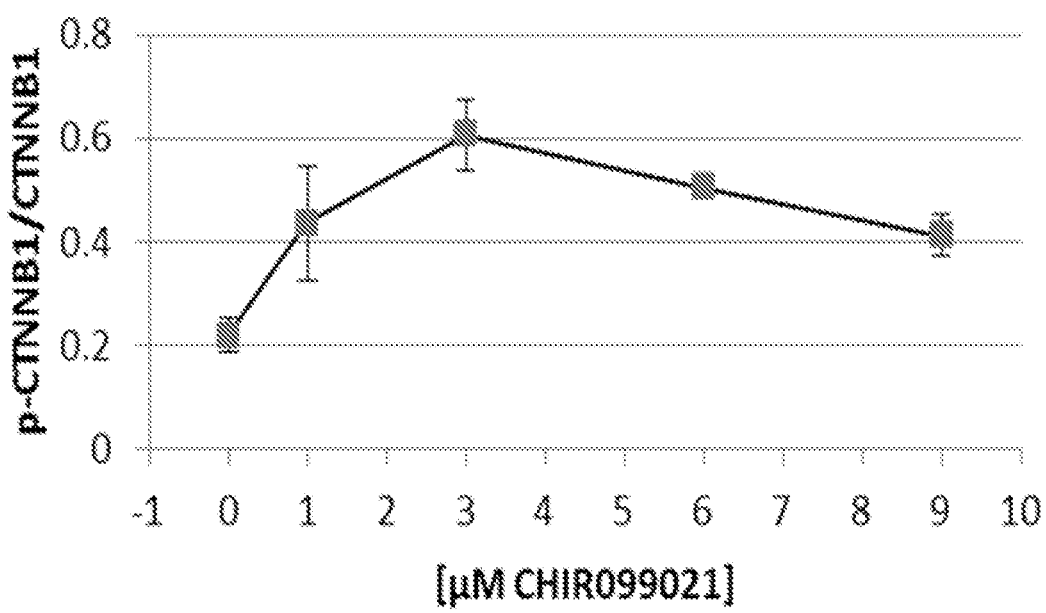
FIG. 13A shows a graph illustrating the densitomentric ratios of p-CTNNB1/CTNNB1 bands as shown in FIG. 12.
Figure 13B:
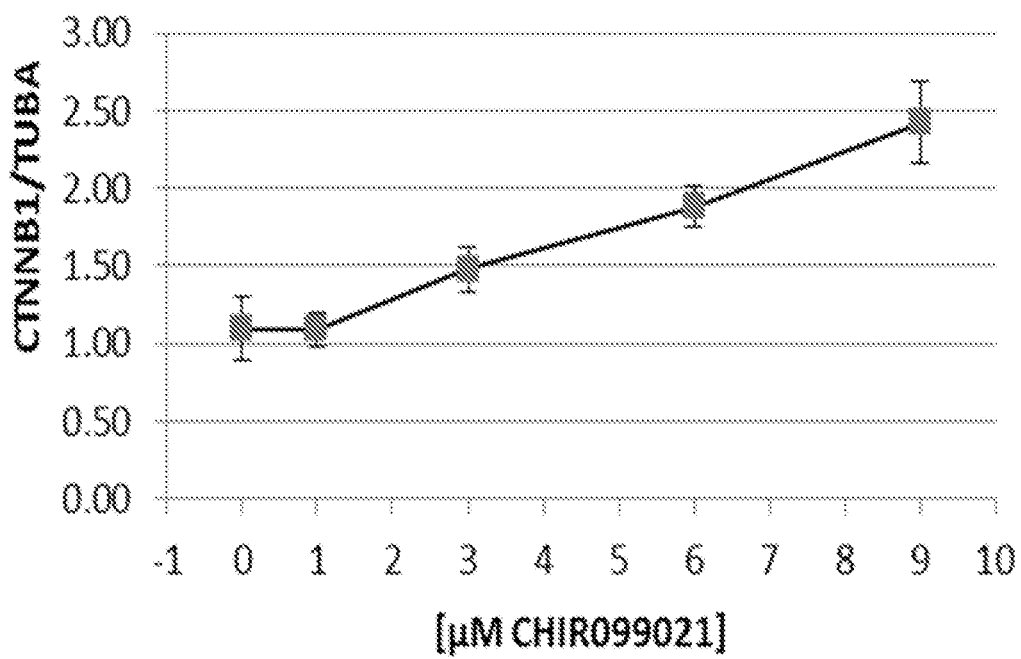
FIG. 13B shows a graph illustrating the densitometric ratios of CTNNB1/TUBA bands as shown in FIG. 12.
Figure 14:
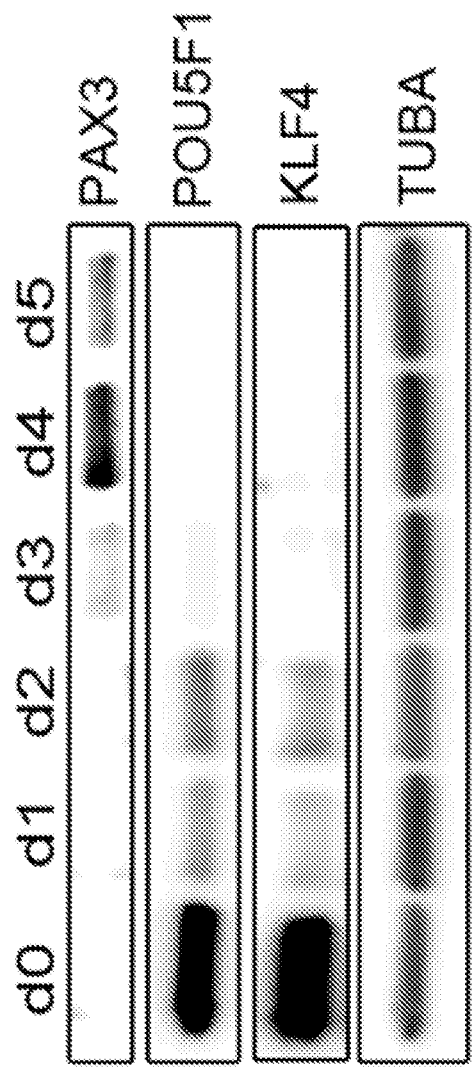
FIG. 14 shows an image illustrating the differentiation marker time-course Western blot analysis. Expression levels of pluripotency markers, POU5F1 and KLF4, and the pre-myogenic paraxial mesoderm marker PAX3 in O2K cultures differentiated from the ground state in the presence of CHIR99021.
Figure 16:
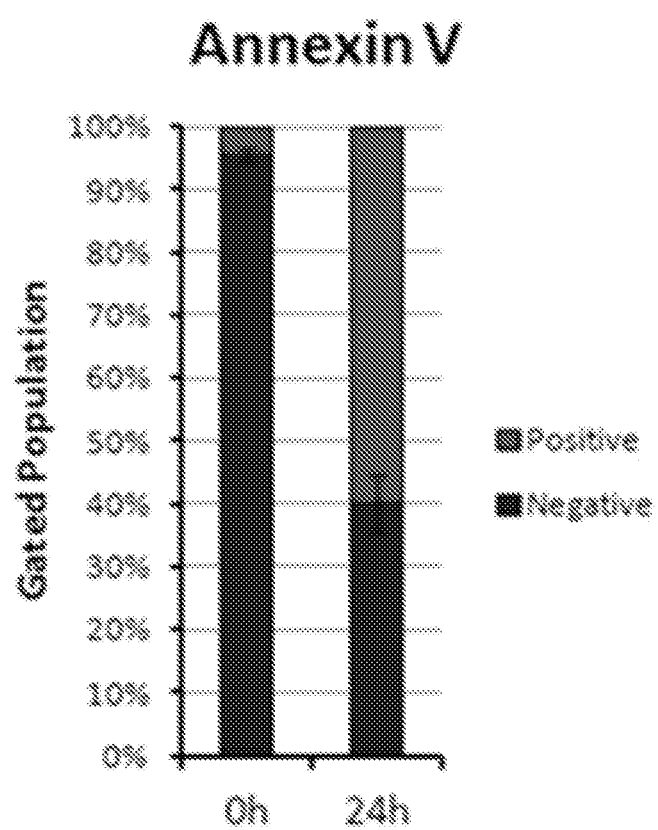
FIG. 16 shows Annexin V labeling of apoptotic cells prior to, and following 24 h transition of cultures, as in FIG. 9, panels i-ii.
Figure 17A:
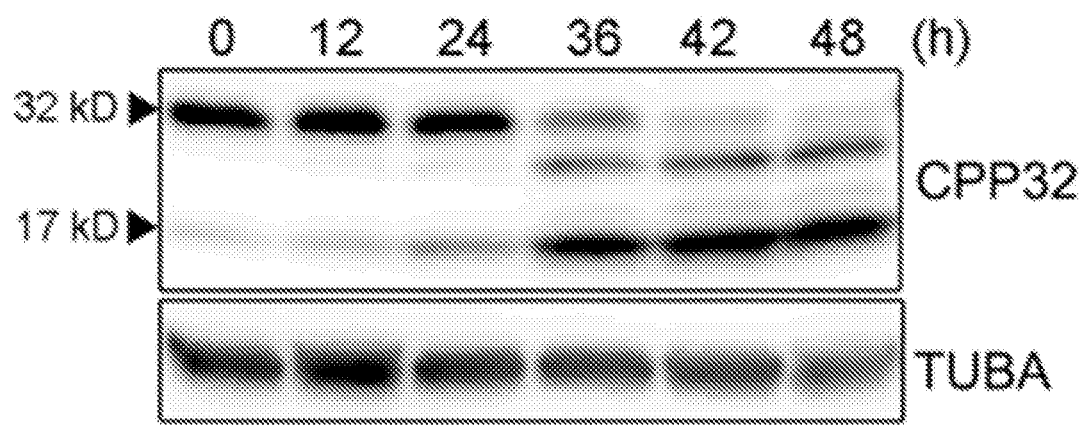
FIG. 17A shows Western blot detection of full-length CPP32 (~32 kD procaspase 3a) and the large cleaved fragment (~17kD cleaved-caspase 3a) in ground-state colonies prior to (0 h) and following (12-48 h) differentiation milieu transition (12-48 h).
Figure 17B:
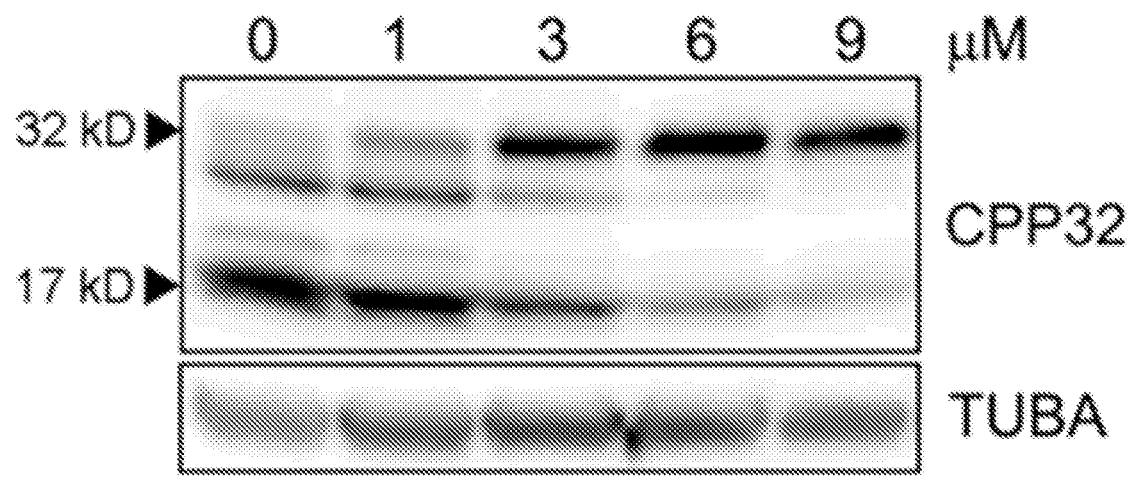
FIG. 17B shows Western blot detection of full-length CPP32 and the cleaved fragment in colonies following 42 h transition to the differentiation milieu in the presence of CHIR99021 levels indicated.

CHIR99021 inhibition of cell death. Differentiation of the parental O2K line in the absence of SRM culture medium components that support self-renewal hLIF, DOX, CHIR99021, PD032591 and PD173074, and KOSR resulted in massive cell death as determined by (1) phase contrast microscopy as shown in FIG. 9, panels i.-ii., (2) CPP32 cleavage, as shown in FIG. 17A, and (3) Annexin V labeling shown in FIG. 16. However, a culture medium formulation including CHIR99021, when retained in the SRM basal medium in the absence of hLIF, DOX, PD032591 and PD173074, supported both cell survival during differentiation as determined by (1) phase-contrast microscopy, as shown in FIG. 9, panels iii.-viii., (2) cell adhesion assay, as shown in FIG. 10, (3) CPP32 cleavage inhibition as shown in FIG. 17B, and (4) Annexin V labeling, as shown in FIG. 11. Moreover, CHIR99021 exposure during primordial differentiation stabilizes and modulates the phosphorylation status of the GSK3 f3 substrate, CTNNB1, as shown in FIGS. 12, 13A and 13B, the phospho-regulated downstream effector of the canonical WNT signaling pathway known to direct mesodermal differentiation during embryonic lineage specification, myogenic enrichment of mesodermal progenitors, and terminal differentiation of skeletal myocytes. Congruent with these findings, CHIR99021 supplemented basal medium supported pre-myogenic paraxial mesoderm lineage specification of differentiating O2K, as shown in FIG. 14 and when included in low-mitogen differentiation cultures (2% horse serum/DMEM) of the myogenic murine C2C12 cell line, enhanced terminal differentiation into skeletal myotubes, listed in Table. 1. As CHIR99021 repressed cell death, supported differentiation toward paraxial mesoderm by the differentiating O2K cell line and enhanced terminal differentiation by the C2C12 cell line, precedent was established to retain the compound in all culture stages. Hence, 3 µM CHIR99021 was retained in the culture medium during expansion, induction and terminal differentiation steps (FIG. 20A) unless stated otherwise.

Figure 6:
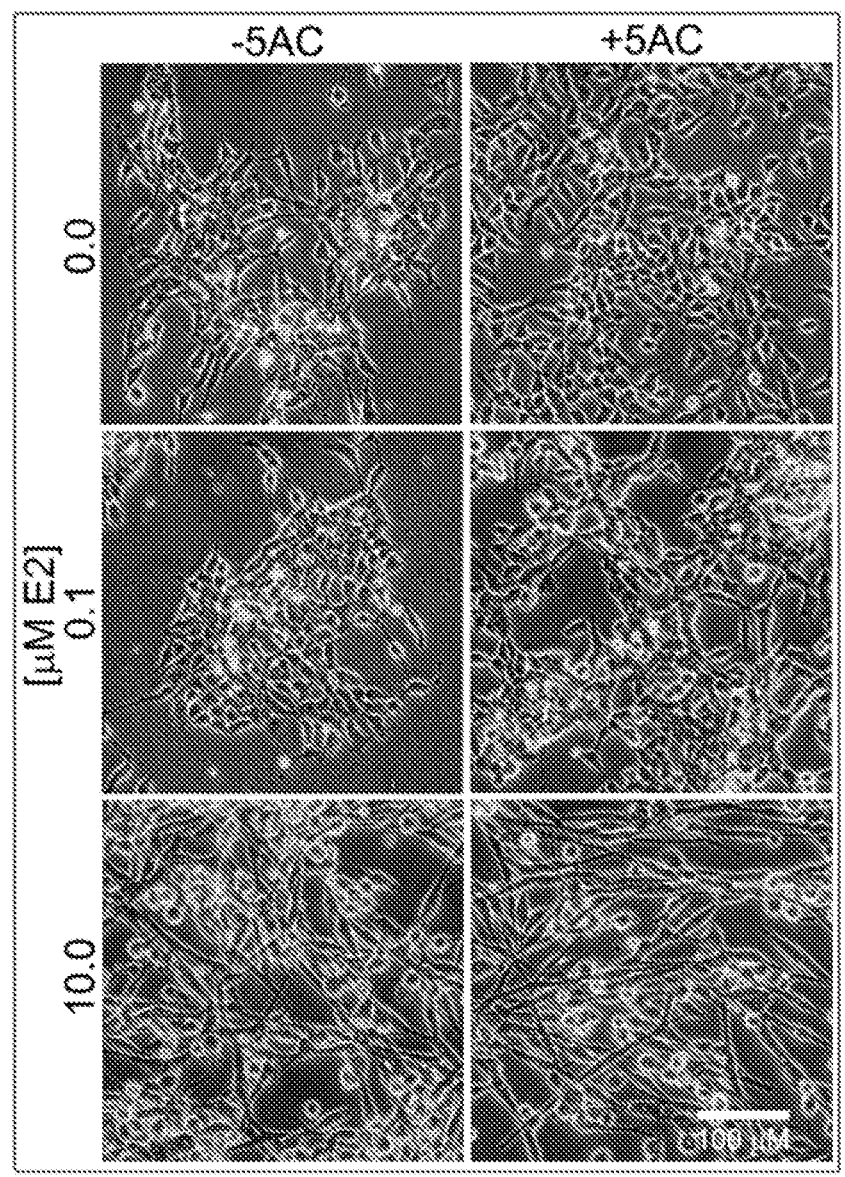
Figure 7:
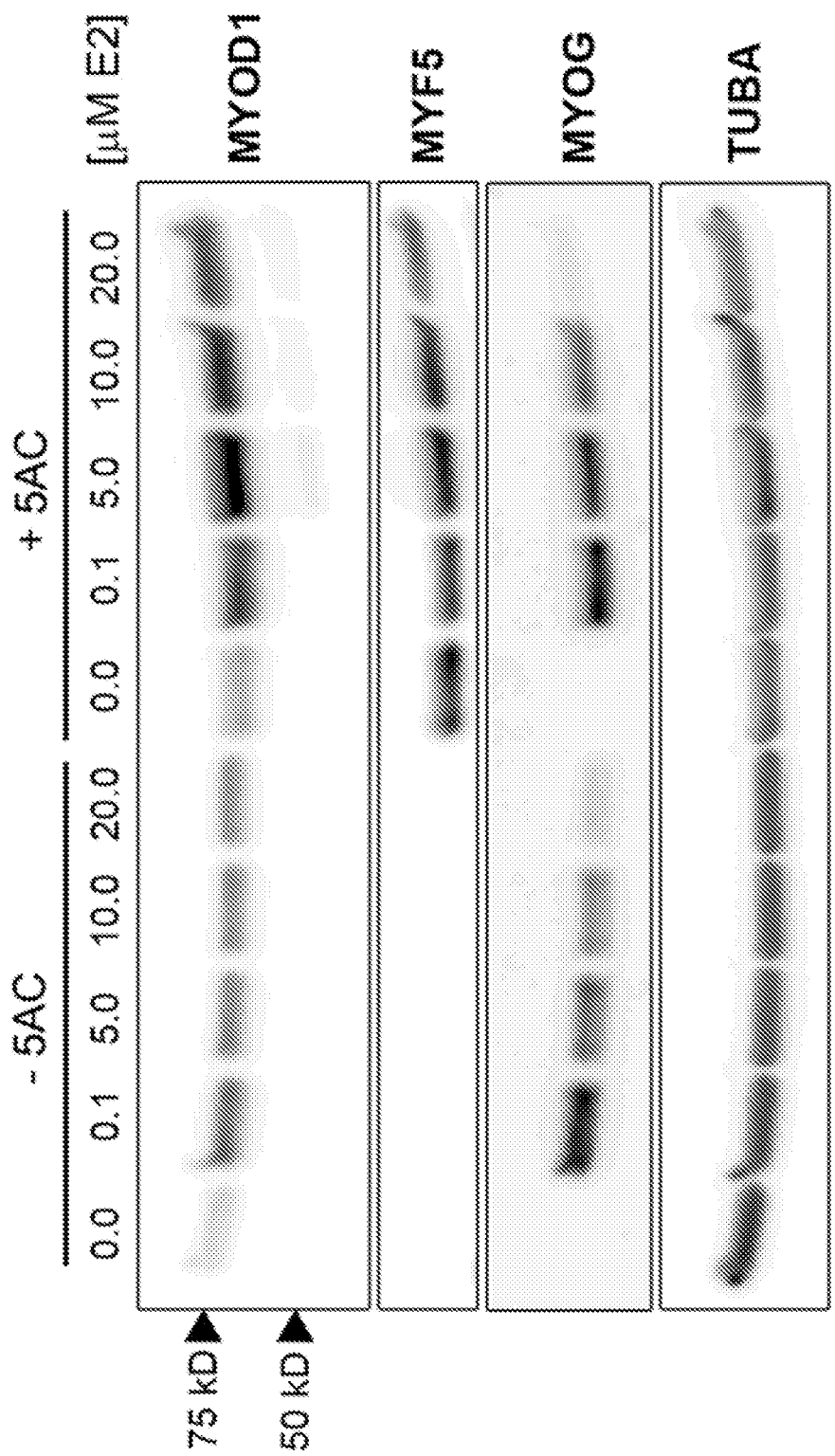
Figure 8:
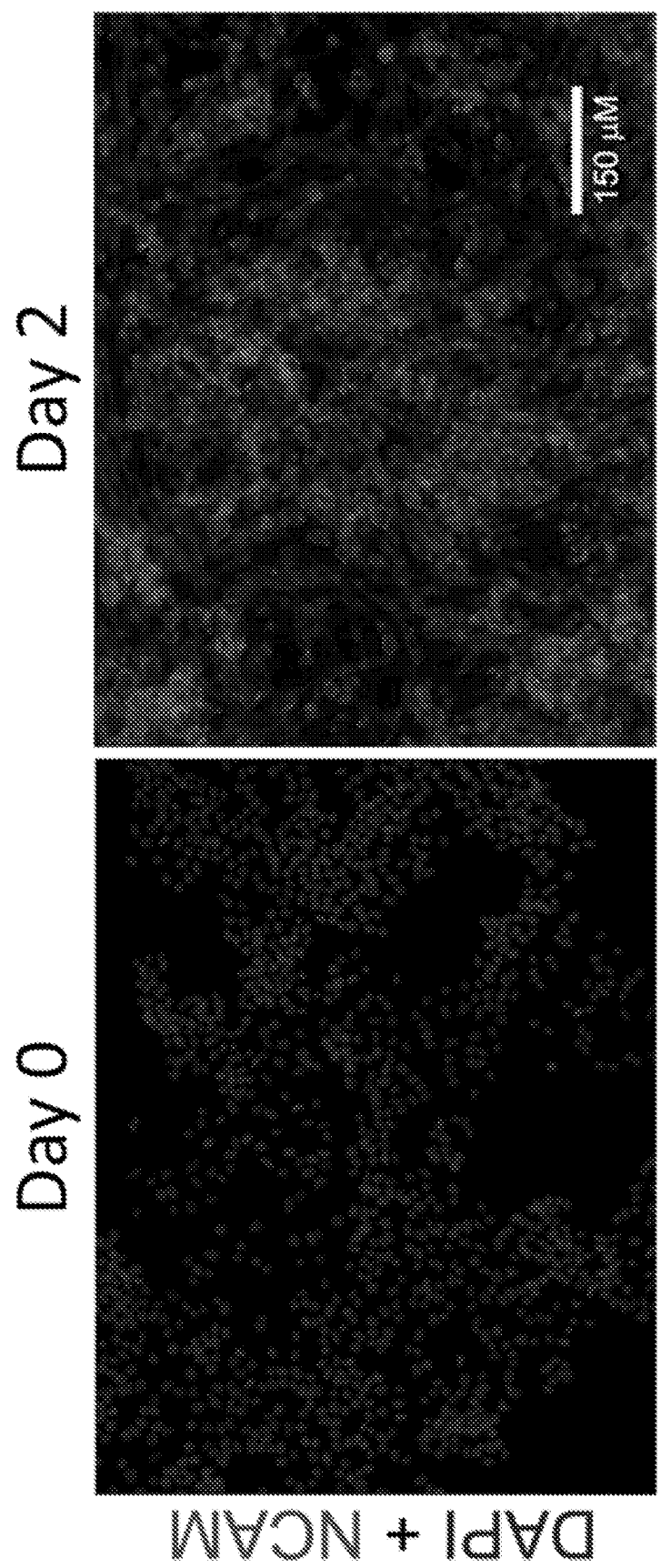

O2KM myogenic induction. O2KM cells were seeded onto culture dishes coated with poly-D lysine, murine laminin and MATRIGEL at a density of $4.1×10^3$ cells/cm² and cultured under 5% $O_2$ in self-renewal medium for 3 d. To facilitate differentiation, cultures were transferred to a 20% $O_2$ basal differentiation milieu, designated by withdrawal of PD032591, PD173074, DOX, hLIF and β-mercaptoethanol. To conditionally induce the expressed MyoDER protein, 10 µM E2 was added to the medium. E2-directed myogenic lineage specification following 2 d induction culture was confirmed by (1) adoption of spindle-like morphology characteristic of skeletal myocytes in treated cultures, as shown in FIG. 6, (2) expression of endogenous the MYOG skeletal muscle transcription factor, as shown in FIG. 7 and (3) uniform expression of the skeletal myocyte cell surface marker, NCAM, as shown in FIG. 8.

Figure 15:
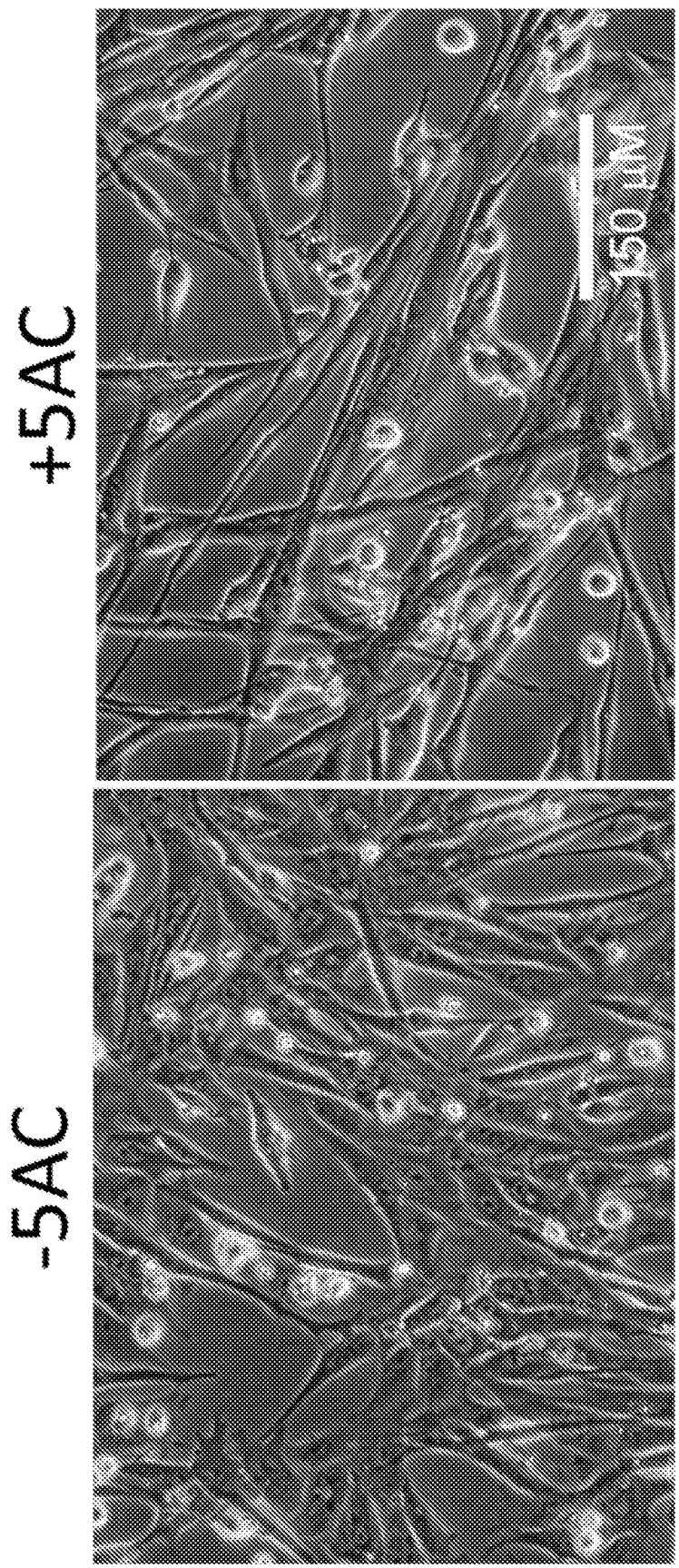
FIG. 15 shows images of terminal differentiation of 02KM myocytes differentiated in the absence (left panel) or presence (right panel) of 5-Aza-Cytidine (5AC). Note the myocyte derivatives with flattened morphology in the left panel (5AC) in contrast to the elongated, multinucleated myotubes in the right panel (+5AC).

5AC effects. 5AC exposure prior to, during, and following E2-mediated induction of 'MyoDER' was introduced to enable terminal-differentiation of O2KM from myocytes into refractive, filamentous myotubes. The murine C2C12 cell line was used as positive control to screen for optimal conditions for terminal differentiation by O2KM. These conditions included: a MATRIGEL extracellular matrix and CHIR99021 supplementation in the absence of E2, as listed in Table 1. However, O2KM-derived myocytes passaged onto MATRIGEL-coated culture dishes in differentiation medium without E2 (the conditions determined optimal for C2C12 terminal differentiation) failed to establish refractive myotubes, as shown in FIG. 15 and FIG. 20B. Hence, the gene expression program in the O2KM-derived myocytes was not sufficient to enable terminal differentiation as per the established conditions. 5AC, a small-molecule epigenetic modulator, was determined previously to enable skeletal muscle transcription in cell lines non-permissive to myogenesis. Moreover, 5AC exposure was further determined to enhance terminal differentiation by the C2C12 cell line. Hence, 250 nM 5AC, the highest dose tolerated by undifferentiated O2KM, was included during in the proliferative O2KM expansion and induction regimens, as shown in FIG. 20A.

Terminal Differentiation. Following 2 d E2 induction, cultures were either terminally differentiated in situ, or passaged to MATRIGEL-coated culture dished in terminal differentiation medium (TDM) at $1.56×10^5$ cells/cm² for terminal differentiation. TDM was formulated from the same components as MIM, except for the following modifications: withdrawal of E2, addition of 4 µM A 83-01, and 100 nM IGF-1. N-2 and B-27 supplements were used exclusively as serum replacements. Cultures were differentiated for up to 6 d following under 20% $O_2$ following induction regimens (FIG. 20A). Cultures exposed to 5AC during expansion and induction regimens formed refractive, anisotropic myotubes during the terminal differentiation regimen, shown in FIG. 20B. FIG. 20C shows uniform expression of myosin heavy chain by d6, and FIG. 20E shows increasing expression of desmin (DES) and myogenin (MYOG) over the 8 d course. Myotube polyploidy was observed during terminal differentiation, as shown in FIG. 20D, left panel. The relative distribution of myonuclei in d8 myotubes according to ploidy is shown in FIG. 20D, right panel. Relative prevalence of S-phase nuclei in the renewal milieu (d3 colonies), expansion milieu (d0 cultures, FIG. 20A), and terminal differentiation milieu (d8 cultures, FIG. 20A), as shown in FIG. 20F, indicated cell cycle withdrawal following terminal differentiation. Contractile potential of terminally differentiating skeletal muscle myotubes was validated by (1) structural development of well-organized sarcomeres, as shown in FIG. 20G; (2) asynchronous spontaneous contraction, as shown in FIG. 21A; (3) contractile stimulation and synchronization by field stimulation, as shown in FIG. 21B; (4) caffeine-stimulated contraction, as shown in FIG. 21C; and (5) acetylcholine-stimulated contraction, as shown in FIG. 21D.

Results

Figure 18:
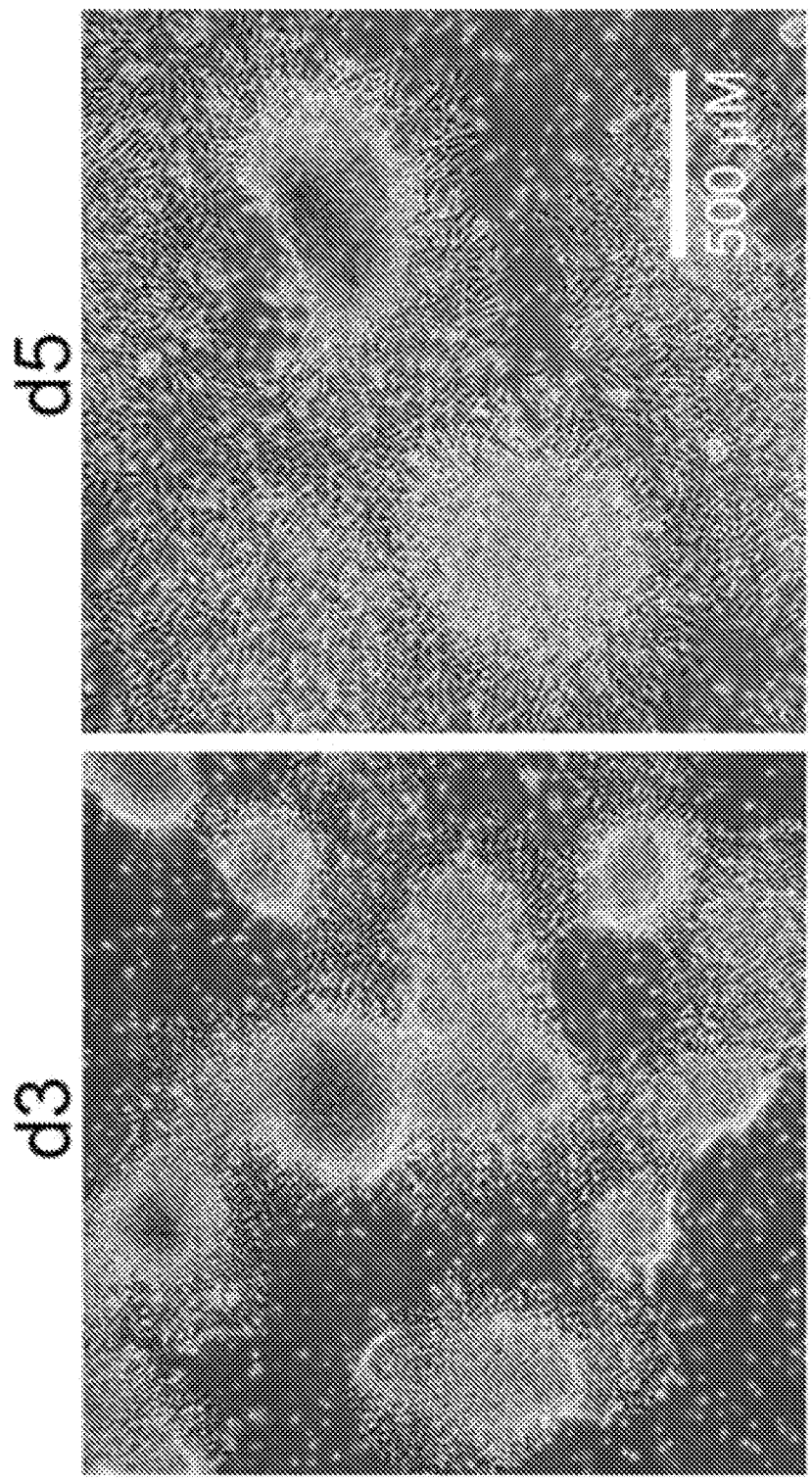
FIG. 18 shows outgrowth morphology of embryoid bodies formed in a differentiation milieu containing 6 µM CHIR99021 for two days and following transfer to a Poly-D Lysine+Laminin+MATRIGEL coated substrate for one (d3, left panel) or three (d5, right panel) additional days.

An axis of apoptosis and differentiation is modulated by CHIR99021. FIG. 9 shows phase-contrast images of ground-state piPSC colonies cultured under 5% $O_2$ in the self-renewal milieu (i.) and following 48 h under 20% $O_2$ in the absence of DOX, LIF and 3i, (ii.). FIG. 16 shows Annexin V labeling of apoptotic cells prior to, and following 24 h transition of cultures. FIG. 17A shows Western blot detection of full-length CPP32 (~32 kD procaspase 3a) and the large cleaved fragment (~17 kD cleaved-caspase 3a) in ground-state colonies prior to (0 h) and following (12-48 h) differentiation milieu transition (12-48 h). FIG. 9 shows phase contrast images of adherent cultures (iii, iv, vi, and vi) and non-adherent embryoid body cultures (vii and viii) following 48 h culture in differentiation milieu supplemented with CHIR99021 as indicated. FIG. 10 shows adherent cell percentage of differentiation milieu cultures supplemented with the CHIR99021 as indicated for 48 h relative to ground-state (i.e. 0 h) cultures, normalized to 100%. *non-adherent cells viable as embryoid bodies. n=3 for each culture condition. FIG. 11 shows Annexin V labeling of apoptotic cells following 24 h transition of cultures to differentiation milieu supplemented with CHIR99021 as indicated. FIG. 17B shows Western blot detection of full-length CPP32 and the cleaved fragment in colonies following 42 h transition to the differentiation milieu in the presence of CHIR99021 levels indicated. TUBA is detected an internal protein loading control. CHIR99021 stabilizes CTNNB1 and supports differentiation from the ground state. FIG. 12 shows Western blot detection of CTNNB1 and p-CTNNB1 (total and phospho-S33,37,T41 β-catenin, respectively) following 24 h differentiation milieu transition in the presence of CHIR99021, as indicated. TUBA detected as an internal protein loading control. FIG. 13A indicates ratios of p-CTNNB1/CTNNB1 bands. FIG. 13B indicates ratios of CTNNB1/TUBA bands. FIGS. 13A and 13B represent densitometric quantitation from Western Blots as shown in FIG. 12; n=3. FIG. 18 shows outgrowth morphology of embryoid bodies formed in a differentiation milieu containing 6 µM CHIR99021 for two days and following transfer to a Poly-D Lysine+Laminin+MATRIGEL coated substrate for one (d3, left panel) or three (d5, right panel) additional days. FIG. 14 shows Western blot analysis of PAX3, POU5F1 and KLF4 expression in ground-state milieu (d0) and differentiation milieu cultures (d1–d5) according to one regimen aspect described elsewhere herein. TUBA detection is shown as an internal protein loading control.

Figures 4A, 4B:
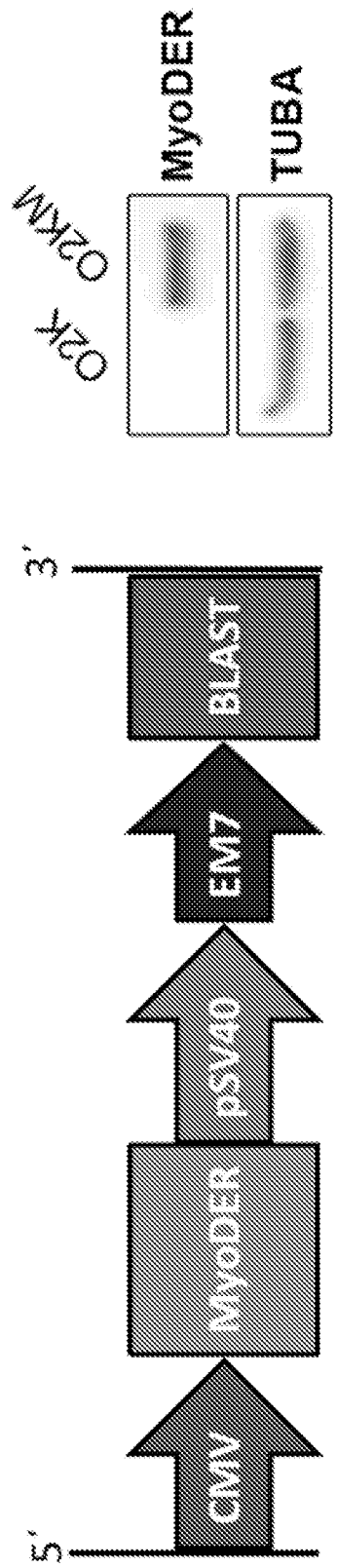
Figure 19A:
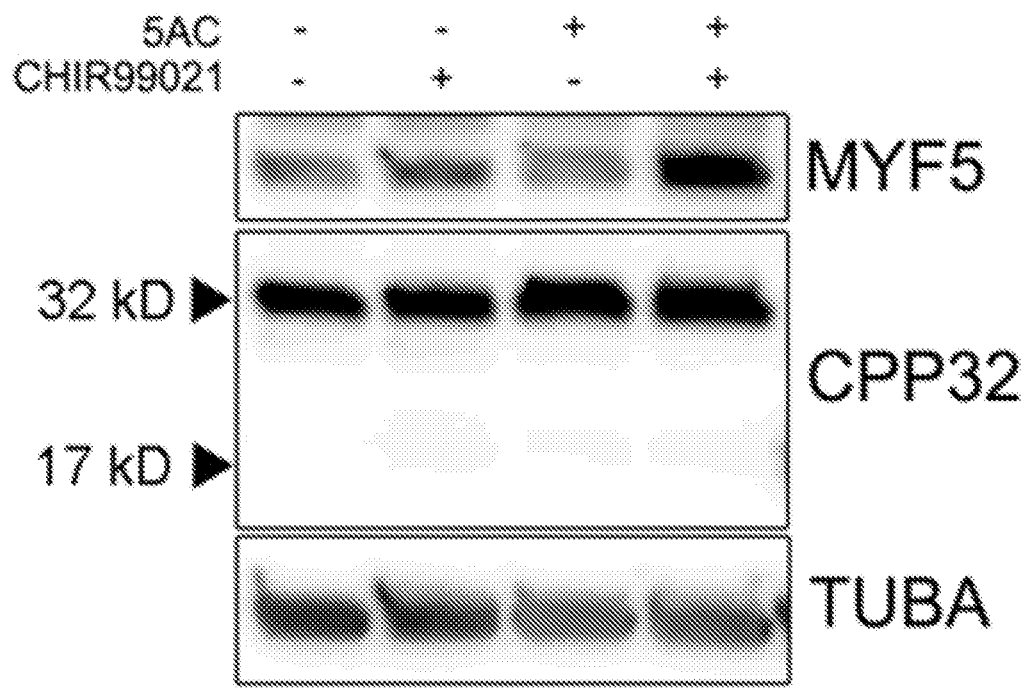
FIG. 19A shows Western Blot of lysates from unmodified piPSC cultured in the absence of 3i, DOX, hLIF and E2 in differentiation milieu containing KOSR.
Figure 19B:
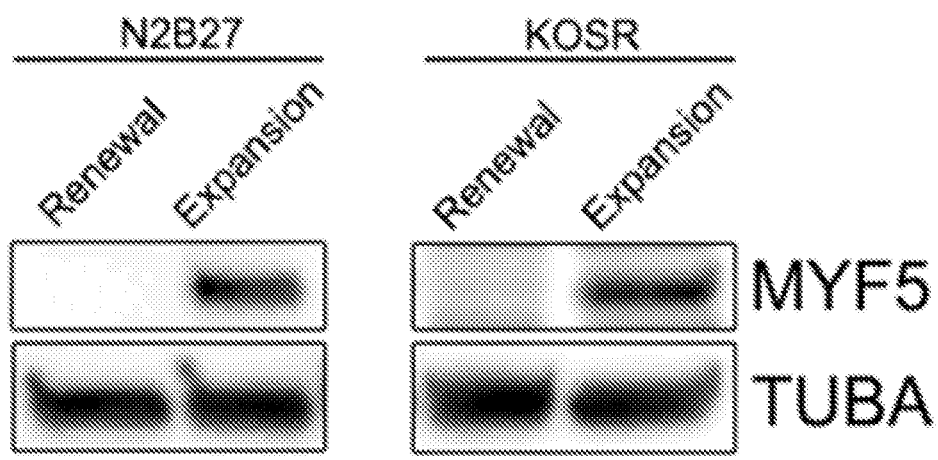
FIG. 19B shows Western Blot of lysates from MyoDER-modified piPSC cultured in the presence of DOX, LIF and 3i. MYODER-modified piPSC were cultured 3 days in self-renewal or expansion milieu.

5-Aza-cytidine and MyoDER activation of endogenous MRFs. piPSC modification with an integrated MyoDER expression cassette. FIG. 4A shows a Blasticidin (BLAST)-selectable MyoDER expression cassette. Arrows and boxes indicate promoter and gene sequences, respectively. FIG. 4B shows Western blot detection of MyoDER in the unmodified (O2K) and MyoDER expression cassette-modified (O2KM) piPSC line. MyoDER was detected with an antibody raised against a MyoD peptide. FIG. 7 shows Western blot detection of MyoDER (~75 kD), MYF5 and MYOG following 2 d piPSC induction. Endogenous MYOD1 (~45 kD, expected) was not detected. O2KM were seeded onto poly-D lysine+Martigel+murine laminin coated culture dishes and cultured with hLIF, 3i & DOX for three days in the presence (i.e. expansion, FIG. 20A) or absence of 5AC, followed by respective transition to a –/+5AC differentiation milieu supplemented with E2 (i.e. 17β estradiol) and 3 µM CHIR99021 for two days. Double Arrow: Partially resolved MYOG isoforms. FIGS. 19A and 19B. Determinants of MYF5 activation: Western blot analyses. FIG. 19A, following three days of culture on poly-d-lysine+laminin+MATRIGEL, unmodified piPSC were cultured 2 d in the absence of 3i, DOX, hLIF and E2 in differentiation milieu supplemented with 5AC (as in FIG. 7) and CHIR99021 as indicated. In the absence of CHIR99021, the 17 kD cleaved caspase isoform was not observed in the KOSR supplemented differentiation milieu, as in contrast to observations in the N-2 and B-27 supplemented differentiation milieu (FIG. 17A, FIG. 19A). 5AC-enhanced activation of endogenous MYF5 expression was dependent upon simultaneous CHIR99021 exposure, as shown in FIG. 19A. FIG. 19B shows MYF5 activation in the presence of DOX, LIF and 3i. MYODER-modified piPSC were cultured 3 days in self-renewal or expansion milieu. In the presence of DOX and CHIR99021, 5AC exposure supported detectable MYF5 expression levels, as shown in FIG. 19B, after 3 days of expansion culture. In contrast MYF5 was not detected following 3 days of renewal culture (–5AC), as shown in FIG. 19B. TUBA is detected as an internal protein loading control. FIG. 6 shows the morphology of selected piPSC cultures following lineage specification induction culture regimens (FIG. 20A) described elsewhere herein. FIG. 8 shows immunocytoflourescent detection of nuclei (DAPI) and NCAM in piPSC-MyoDER cultures prior to (d0, left panel) and following (d2, right panel) 10 µM E2 exposure, in the presence of 5AC.

Terminal Myogenesis of Lineage-Specified piPSC. Prior to terminal differentiation, cultures were expanded for 3 days in the presence of 5AC, induced for 2 days in the presence of E2 & 5AC, and terminally differentiated in the absence of 5AC & E2 as shown in FIG. 20A. FIG. 20B shows myotube morphology and conformation. Post-induction (d2), piPSC developed as elongated, anisotropic, refractive myotubes. Where 5AC was not included in the expansion and induction steps, cells exhibited a flattened, non-refractive morphology. FIG. 20C and FIG. 20E show terminal myogenesis protein expression. D0 and D6 cultures were stained for myosin heavy chain (MyHC) isoforms with a pan-MyHC monoclonal antibody, clone MF20. FIG. 20D shows myotube multinucleation. Left panel: enlarged image of d4 terminal differentiation cultures. Bracketed arrows indicate multiple nuclei within a single myotube. Right panel: myonuclei distribution by myotube ploidy by propidium iodide labeling and flow cytometry analysis. n=3 with standard deviation shown. FIG. 20E shows Western blot analyses. MyoD (MYOD1), myogenin (MYOG) and desmin (DES) expression, d0-d8. TUBA is detected as an internal protein loading control. FIG. 20F shows cell-cycle withdrawal coinciding with terminal differentiation. d3 modified piPSC renewal, expansion cultures and d8 terminal differentiation cultures were labeled with EdU, and the S-phase fraction was determined by flow cytometry. n=3 with standard deviation shown. FIG. 20G: Transmission Electron Microscopy, d6 myotubes. Sarcomeric structural units were aligned in single (left panels) and staggered, parallel rows (right panel).

Spontaneous and Stimuli-Induced Calcium Transient Activity in piPSC-derived myotubes. To quantify contraction cycles, myotube cultures were stained with Fluo-4 AM calcium dye, washed, and image sequences were captured by confocal microscopy. Dynamic signaling events of an entire field of view (FOV) or single cells were traced and plotted over the imaging course. [s]=seconds. FIG. 21A shows representative asynchronous, single-cell transient cycles (left, middle and right panels) were observed in spontaneously contracting d6 myotube subpopulations. FIG. 21B shows FOV activation and synchronization of calcium transient cycles by 1.0 Hz field stimulation in d6 myotubes. FIG. 21C shows FOV calcium transient activation of d6 myotubes by 10 mM caffeine. FIG. 21D: single-cell analysis of representative calcium transient activation in a d7 myotubes by 100 nM acetylcholine.

Discussion

In summary, it has been discovered that certain aspects of the exemplary embodiments described in this disclosure demonstrate one or more of the following unexpected advantages for cultured meat applications:
(i) Rapid Cell Proliferation Rate;
(ii) Rapid Differentiation: With as little as 48 hours of 17β-estradiol induced MyoDER activation and doxycycline withdrawal, the O2KM cell line differentiates to the myogenic lineage, in vitro. No lengthy differentiation procedures required;
(iii) Efficient Differentiation: The CHIR99021/5AC/MyoDER-directed lineage specification ensures extensive high-fidelity conversion to functional skeletal myocytes. No cell sorting is required;
(iv) Infinite Self-Renewal: Self-renewal of undifferentiated O2KM is tightly enforced supported in the self-renewal milieu;
(v) Self-Renewal and Terminal Differentiation in Serum-Free Medium: Self-renewal and terminal myogenic differentiation of the O2KM line were both validated in serum-free medium;
(vi) Compatible with Suspension Culture Systems as Embryoid Bodies: In the pluripotent state, the parental O2K and modified O2KM are resistant to anoikis and may be cultivated into embryoid bodies from single cells in suspension culture. O2KM-derived embryoid bodies may be compatible with multiceluar spheroid assembly technologies such as bioprinting and mircomolds for cultured meat production; and
(vii) Autologous Contraction: O2KM terminally differentiated as skeletal muscle exhibits sarcomeric maturation and autologous contraction. Hence, external stimulation (e.g. mechanical tension, acetylcholine receptor activation, electrical stimulation) may not be necessary to promote myofiber maturation.

While the invention has been described in connection with example embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. An in vitro method for producing a cultured meat product for dietary consumption, the method comprising:
   modifying a porcine induced pluripotent stem cell line comprising pluripotency genes POU5F1 and KLF4 with an inducible MYOD1 transcription factor to produce an inducible MYOD1-transcription-factor-modified porcine cell line;
   inducing myogenic differentiation of said modified cell line by exogenous regulation, comprising contacting said modified cell line with an activator of canonical WNT signaling, an inducer of MYoD1 expression, and an inhibitor of DNA methylation, wherein the inhibitor is 5-Aza-Cytidine or 5-Aza-2'-deoxycytidine, wherein the differentiated modified cell line forms myocytes and multinucleated myotubes, both comprising myonuclei, and wherein greater than 50% of the total myonuclei are within the multinucleated myotubes; and
   culturing the myocytes and multinucleated myotubes to generate skeletal muscle fibers, thereby producing a cultured meat product for dietary consumption.

2. The method of claim 1 comprising: maintaining the modified cell line in a first culture medium for undifferentiated cell stock expansion prior to inducing myogenic differentiation in a second culture medium.

3. The method of claim 2, wherein the modified cell line comprises the pluripotency genes POU5F1 and KLF4 operably linked to a tetracycline responsive element and a tetracycline transactivator, and wherein the first culture medium comprises doxycycline.

4. The method of claim 2, wherein the inducing myogenic differentiation comprises transferring the modified cell line from the first culture medium to the second culture medium for myogenic differentiation, wherein the 5-Aza-Cytidine or 5-Aza-2'-deoxycytidine is present in the second culture medium.

5. The method of claim 4, wherein the modified cell line comprises a chromosomally integrated vector constitutively expressing an inducible fusion of MYOD1 transcription factor and an ESR1 ligand binding domain, and wherein the second culture medium comprises an ESR1 agonist.

6. The method of claim 5, wherein the ESR1 agonist is 17-β estradiol (E2).

7. The method of claim 4, wherein said second culture medium comprises the activator of canonical WNT signaling.

8. The method of claim 7, wherein the activator of canonical WNT signaling comprises a GSK3β inhibitor.

9. The method of claim 8, wherein said GSK3β inhibitor is selected from one or more members of the group consisting of CH1R99021, lithium chloride, 6-bromoindirubin-3'-oxime (BIO), SB216763, CHIR-98014, TWS119, Tideglusib, IM-12, 1-Azakenpaullone, AR-A014418, and SB415286.

10. The method of claim 9, wherein said GSK3β inhibitor is CHIR99021.

11. A cultured meat product for dietary consumption produced by the in vitro method of claim 1, wherein the skeletal muscle fibers comprise an inducible vector encoding a MYOD1 myogenic transcription factor.

* * * * *